US006900285B2

(12) United States Patent
Woo et al.

(10) Patent No.: US 6,900,285 B2
(45) Date of Patent: May 31, 2005

(54) FLUORENE-CONTAINING POLYMERS AND COMPOUNDS USEFUL IN THE PREPARATION THEREOF

(75) Inventors: Edmund P. Woo, Midland, MI (US); William R. Shiang, Sanford, MI (US); Michael Inbasekaran, Midland, MI (US); Gordon R. Roof, Midland, MI (US); Mark T. Bernius, Midland, MI (US); Weishi Wu, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 102 days.

(21) Appl. No.: 10/318,579

(22) Filed: Dec. 13, 2002

(65) Prior Publication Data

US 2003/0208032 A1 Nov. 6, 2003

Related U.S. Application Data

(63) Continuation of application No. 09/661,237, filed on Sep. 13, 2000, now Pat. No. 6,512,083, which is a continuation of application No. 08/861,469, filed on May 21, 1997, now Pat. No. 6,169,163, which is a continuation-in-part of application No. 08/508,942, filed on Jul. 28, 1995, now Pat. No. 5,708,130, and a continuation-in-part of application No. 08/508,943, filed on Jul. 28, 1995, now abandoned.

(51) Int. Cl.[7] .............................................. C08G 75/00
(52) U.S. Cl. ........................ 528/373; 528/394; 528/397
(58) Field of Search ................................ 528/373, 394, 528/397

(56) References Cited

U.S. PATENT DOCUMENTS

| | | | |
|---|---|---|---|
| 3,641,115 A | 2/1972 | Peck et al. .................. 260/475 |
| 4,539,507 A | 9/1985 | VanSlyke et al. ........... 313/504 |
| 4,769,292 A | 9/1988 | Tang et al. .................. 428/690 |
| 4,983,482 A | 1/1991 | Ong et al. ..................... 430/59 |
| 5,247,190 A | 9/1993 | Friend et al. ................. 257/40 |
| 5,298,189 A | 3/1994 | Kauffman .............. 252/301.17 |
| 5,304,688 A | 4/1994 | Bowman et al. ............ 568/727 |
| 5,386,002 A | 1/1995 | Inbasekaran ................ 528/170 |
| 5,399,502 A | 3/1995 | Friend et al. .................. 437/1 |
| 5,401,827 A | 3/1995 | Holmes et al. ............. 528/374 |
| 5,447,960 A | 9/1995 | Sinnott et al. .............. 514/732 |
| 5,621,131 A | 4/1997 | Kreuder et al. .............. 558/46 |
| 5,679,760 A | 10/1997 | Mullen et al. .............. 528/220 |
| 5,682,043 A | 10/1997 | Pei et al. ...................... 257/40 |
| 5,708,130 A | 1/1998 | Woo et al. .................. 528/397 |
| 5,728,801 A | 3/1998 | Wu et al. .................... 528/422 |
| 5,756,804 A | 5/1998 | Haber et al. ................ 558/411 |
| 5,777,070 A * | 7/1998 | Inbasekaran et al. ....... 528/394 |
| 5,801,263 A | 9/1998 | Seitz et al. .................. 558/155 |
| 5,807,974 A | 9/1998 | Kim et al. ................... 528/366 |
| 5,814,244 A | 9/1998 | Kreuder et al. ........ 252/301.16 |
| 5,858,563 A | 1/1999 | Sano et al. .................. 428/690 |
| 5,876,864 A | 3/1999 | Kim et al. ................... 428/690 |
| 5,879,821 A | 3/1999 | Hsieh ......................... 428/690 |
| 5,900,327 A | 5/1999 | Pei et al. ..................... 428/690 |
| 5,929,194 A | 7/1999 | Woo et al. .................. 528/229 |
| 5,962,631 A | 10/1999 | Woo et al. .................. 528/397 |
| 5,998,045 A | 12/1999 | Chen et al. ................. 428/690 |
| 6,140,265 A | 10/2000 | Haber et al. ................ 502/162 |
| 6,169,163 B1 | 1/2001 | Woo et al. .................. 528/397 |
| 6,255,447 B1 | 7/2001 | Woo et al. .................. 528/397 |
| 6,255,449 B1 | 7/2001 | Woo et al. .................. 528/401 |
| 6,309,763 B1 | 10/2001 | Woo et al. .................. 428/690 |
| 6,353,083 B1 | 3/2002 | Inbasekaran et al. ....... 528/295 |
| 6,362,310 B1 | 3/2002 | Woo et al. .................. 528/397 |
| 6,512,083 B1 | 1/2003 | Woo et al. .................. 528/397 |
| 6,514,632 B1 | 2/2003 | Woo et al. .................. 428/690 |
| 6,593,450 B2 | 7/2003 | Woo et al. .................. 528/397 |
| 6,605,373 B2 | 8/2003 | Woo et al. .................. 428/690 |

FOREIGN PATENT DOCUMENTS

| | | | |
|---|---|---|---|
| EP | 0 707 020 | 4/1996 | .......... C08G/61/00 |
| FR | 2702870 | 9/1994 | ............ G09F/9/30 |
| JP | 04221328 A | 8/1992 | .......... C07C/25/22 |
| WO | WO 94/24079 | 10/1994 | .......... C07C/37/20 |
| WO | WO 95/01871 | 1/1995 | ........... B32B/15/04 |
| WO | WO 96/00983 | 1/1996 | ........... H01L/35/24 |
| WO | WO 97/05104 | 2/1997 | ........ C07C/253/30 |
| WO | WO 97/05184 | 2/1997 | .......... C08G/61/10 |
| WO | WO 97/33193 | 9/1997 | |
| WO | WO 97/39045 | 10/1997 | .......... C08G/61/00 |
| WO | WO 97/39082 | 12/1997 | .......... H05B/33/04 |

OTHER PUBLICATIONS

Grell et al., Monodomain alignment of thermotropic fluorene copolymers, 1999, Taylor & Francis Ltd., Chem Abstract 131: 305082.*

Ranger et al., Opticla and electrical properties of fluorene based –conjugated polymers, 1998, National Research Council of Canada, Chem Abstract 131:282433.*

(Continued)

*Primary Examiner*—Duc Truong
(74) *Attorney, Agent, or Firm*—Susan Moeller Zerull

(57) ABSTRACT

A polymer comprising repeat units of the formula:

$$\left[ \begin{array}{c} (R^2)_a \quad (R^2)_a \\ \phantom{xxx} \\ \phantom{xxx} \\ R^1 \quad R^1 \end{array} \left( \begin{array}{c} \phantom{x} \\ S \end{array} \right)_m \right]_n$$

wherein $R^1$ is independently in each occurrence $C_{1-20}$ hydrocarbyl or C1–20 hydrocarbyl containing one or more heteroatoms of S, N, O, P or Si or both $R^1$ may form, with the 9-carbon of the fluorene ring, a $C_{5-20}$ ring structure containing one or more heteroatoms of S, N, or O; $R^2$ is independently in each occurrence $C_{1-20}$ hydrocarbyl, $C_{1-20}$ hydrocarbyloxy, $C_{1-20}$ thioether, $C_{1-20}$ hydrocarbyloxycarbonyl, hydrocarbylcarbonyloxy, or cyano; a is independently in each occurrence a number from about 0 to about 1;
m is a number from about 1 to about 2; and
n is a number from about 3 or greater.

6 Claims, No Drawings

OTHER PUBLICATIONS

Adachi et al., "Blue Ligh–Emitting Organic Electroluminescent Devices," *Applied Physics Letters*, vol. 56, No. 9; pp. 799–801, Feb. 26, 1990.

*Advanced Organic Chemistry: Reactions, Mechanisms and Structures*, 3$^{rd}$ Ed., Jerry March, John Wiley & Sons, pp. 484, 601, 648, 845, 990–991, and 1103 (1985).

Archer et al., "Electrochemical Reactions. Part VI—Application of the Hammett Relationship to the Polargraphic Reduction of Substituted 9–Benzylidenefluorenes and 3–Phenylcoumarins," J. Chem. Soc. (B), pp. 266–270 (1969).

Babb, et al., *ACS Polymer Preprints*, vol. 34(1), p. 413 (1993).

Bradley, D. D. C., et al., "Electro–Optic Properties of Precursor Rout Poly(arylene vinylene) Polymers," *Springer Series in Solid–State Sciences*, vol. 107, pp. 304–309 (1992).

Braun, D., et al., "Visible Light Emission From Semiconducting Polymer Diodes," *Appl. Phys. Lett.*, vol. 58, No. 18, pp. 1982–1984 (May 6, 1991).

Brown, Charles Eric, "Polynuclear and Halogenated Structures in Polyphenylenes Synthesized from Benzene, Biphenyl, and p–Terphenyl Under Various Conditions: Characterization by Laser Desorption/Fourier Transform Mass Spectrometry," *Journal of Polymer Science: Polymer Chemistry Edition*, vol. 24, pp. 255–267 (1986).

Burroughes, et al, "Light–Emitting Diodes Based on Conjugated Polymers," *Nature*, vol. 347, pp. 539–541 (1990).

Burrows et al., "Metal Ion Dependent Luminescence Effects in Metal Tris–Quinolate Organic HEterojunction Light Emitting Devices," *Applied Physics Letters*, vol. 64, pp. 2718–2720 (May 16, 1994).

Chemical Abstract 59, 15231 (1963).

Chemical Abstracts 67, 64085x, Bull. Acad. Pol. Sci. Chim. 15(4), 165–7 (1967).

Chemical Abstract 126:322721 (1997).

Cho et al., "Blue and Green Light Emission from New Soluble Alternating Copolymers," *Advanced Materials*, vol. 9, No. 4, pp. 326–328 (1997).

Cho et al., "Synthesis and Characterization of Soluble Blue Light Emitting Alternating Copolymer," *Macromol. Symp.*, vol. 125, pp. 133–142 (1997).

Colon et al., "Coupling of Aryl Chlorides by Nickel and Reducing Metals," *Journal of Organic Chemistry*, vol. 51, pp. 2627–2637 (1986).

Colon et al., "High Molecular Weight Aromatic Polymers by Nickel Coupling of Aryl Polychlorides," *Journal of Polymer Science, Part A. Polymer Chemistry*, vol. 28, pp. 367–383 (1990).

"Crosslinkable Branched Polyarylamines", filed in the United States of America on Aug. 13, 1996, U.S. Appl. No. 08/696,280; Applicants: E.P. Woo et al.—Now Abandoned. Derwent 94–307586/38 (JP 06234668–A), p. 119, Week 9438.

Fuji et al., "Color–Variable Electroluminescent Diode with Single Quantum Well Structure Utilizing 8–Hydroxyquinoline Aluminum and Aromatic Diamine," *Jpn. J. Appl. Phys.*, vol. 34, pp. 499–502, 1995.

Fukuda et al., "Fusible Conducting Poly(9–alkylfluorene) and Poly(9,9–dialkylfluorene) and Their Characteristics," *Jpn. J. Appl. Phys.*, vol. 28, No. 8, pp. 1433–1435, 1989.

Fukuda et al., "Synthesis of Fusible and Soluble Conducting Polyfluorene Derivatives and Their Characteristics," *Journal of Polymer Science: Part A: Polymer Chemistry*, vol. 31, pp. 2465–2471, 1993.

Ghera et al., "Reactions of Active Methylene Compounds in Pyridine Solution. II. Aldol–type Reactions of Indene and Fluorene," *Journal of American Chemical Society*, vol. 82, pp. 4945–4952 (1960).

Grem, G., et al., "Realization of a Blue–Light–Emitting Device using Poly(p–phenylene)", *Advanced Materials*, vol. 4, pp. 36–37 (1992).

Grice, et al., "High brightness and efficiency blue light–emitting polymer diodes," *Applied Physics Letters*, vol. 73, No. 5, pp. 629–631 (1998).

Gupta et al., "Studies on Ylids: Isolation & Reactions of a New Stabilized Phosphonium Ylid," Indian J. Chem., vol. 20B (1981).

Hallas et al., "Extended Conjugation in Di– and Tri–arylmethanes. Part I. Electronic Absorption Spectra of 9,9–Dimethylfluorene Analogues of Crystal Violet and Malachite Green," Phys. Org., pp. 975–979 (1969).

Hamada et al., "Organic Electroluminescent Devices with Bright Blue Emission," *Optoelectronics–Devices and Technologies*, vol. 7, No. 1, pp. 83–93 (Jun. 1992).

Hamada et al., "High Luminance in Organic Electroluminescent Devices with Bis(10–hydroxybenzo[h]quinolinato-)beryllium as an Emitter," *Chemistry Letters*, pp. 905–906 (1993).

Hayes, et al., "2,5–Diaryloxazoles and 2,5–Diaryl–1,3,4,–oxadiazoles," *J. Amer. Chem. Soc.*, vol. 77, p. 1850 (1955).

Hergenrother, "Reactive Oligomers," *ACS Smposium Series 282*, American Chemical Society, Washington D.C., p. 1 and Percec, et al, p. 91 (1985).

Ioyda et al., "Homocoupling of Aryl Halides Using Nickel(II) Complex and Zinc in the Presence of Et$_4$NI. An Efficient Method for the Synthesis of Biaryls and Bipyridines," *Bulletin of the Chemical Society of Japan*, vol. 63, pp. 80–87 (1990).

Kauffman et al., "Synthesis and Photophysical Properties of Fluorescent 2–Aryl–1,3–dialkylbenzimidazolium Ions and a 1–Alkyl–2–arylbenzimidazole with Excited State Intramolecular Proton–Transfer," J. Heterocyclic Chem., vol. 31, pp. 957–965 (1994).

Kido, et al., "Single–Layer White Light–Emitting Organic Electroluminescent Devices Based on Dye–Dispersed Poly(N–vinylcarbazole)," *Appl. Phys. Lett.*, vol. 67, No. 16, pp. 2281–2283 (1995).

Kido et al., "Blue Electroluminescent 1,2,4–Triazole Derivative," *Chemistry Letters*, pp. 47–48 (1996).

Kim et al., "Characteristics of an Emissive Polymer Blend on LED," *Polym. Prepr.*, vol. 38, No. 1, pp. 417–418 (1997).

Larmat et al., "Electrochemical and Electronic Properties of Poly[bis(2–thienyl)–9,9'–didecylfluorene] and Poly[bis(2–(3,4–ethylenedioxy)thienyl)–9,9'didecylfluorene]," *Amer. Chem. Soc.*, vol. 37, No. 1, pp. 799–800, 1997.

LeDeit et al., "Anodic oxidation of bis(9,9–B–cyanoethyl)fluorine: an efficient way for synthesizing a new functionalizable conducting polymer," *Synthetic Metals*, vol. 47, pp. 373–376, 1992.

Li et al., "Synthesis and Optoelectronic Properties of Aromatic Oxadiazole Polymers," *Journal of Chemical Society*, pp. 2211–2212 (1995).

Miyaura et al., "Palladium–Catalyzed Cross–Coupling Reactions of Organoboron Compounds," *Chemical Reviews*, vol. 95, pp. 2457–2483 (1995).

Miyaura et al., "The Palladium–Catalyzed Cross–Coupling Reaction of Phenylboronic Acid with Haloarenes in the Presence of Bases," *Synthetic Communications*, vol. 11, No. 7, pp. 513–519 (1981).

O'Brien et al., "Electroluminescence applications of a poly(phenyl quinoxalline)," *Synthetic Metals*, vol. 76, pp. 105–108 (1996).

Ohmori et al., "Visible–Light Electroluminescent Diodes Utilizing Poly(3–alkylthiophene)," *Jpn. J. of Appl. Phys.*, vol. 30, No. 11B, pp. L1938–L1940 (1991).

Ohmori et al., "Carrier transport in a three–layered electroluminescent device," *J. Phys. D: Appl. Phys.*, vol. 29, pp. 2983–2987 (1996).

Ohmori et al., "Enhancement of Emission Efficiency in Electroluminescent Diode Utilizing Vapor–Deposited Poly–(alkylfluorene)," *Jpn. J. Appl. Phys.*, vol. 32, No. 11B, pp. 1663–1666 (1993).

Orlando, et al., "Red– and Near–infrared–luminescent Benzazole Derivatives," *Chem. Commun.*, p. 1551–1552 (1971).

Ott, et al., Liquid Scintillators. XII. Absorption and Fluorescence Spectra of 2,5–Diaryl–1,3,4–oxadiazoles, *J. Org. Chem.* vol. 25, p. 872 (1959).

Pai et al., "Trap–Controlled Hopping Transport," *J. Ph ys. Chem.*, vol. 8, pp. 4714–4717 (1984).

Percec et al., "Synthesis of Functional Poly(p–phenylene)s from Substituted Hydroquinones via Nickel–Catalyzed Coupling of Their Bistrifilates," *Macromolecules*, vol. 25, pp. 1816–1823 (1992).

Pettit et al., "Conversion of Cyclohexanone to Spiro[3,4–cyclohexano–4–hydroxybicyclo[3.3.1]nonan–9–one2,1'–cyclohexane]," *J. Org. Chem.*, vol. 46, No. 21, pp. 4167–4171 (1981).

Pomerantz et al., *Amer. Chem. Soc. Polymer Preprints*, vol. 35, No. 1, pp. 210–211 (1994).

Rehahn et al., "Soluble poly(para–phenylene)s. 1. Extension of the Yamamoto synthesis to dibromobenzenes substituted with flexible side chaings," *Polymer*, vol. 30, pp. 1054–1059 (1989).

Remmers et al., "Synthesis, optical absorption and fluorescence of new poly(p–phenylene)–related polymers," *Macromolecular Rapid Communications*, vol. 17, pp. 239–252 (1996).

Schiavon et al., "Anodic and Cathodic Deposition of Electroactive Polyfluorene Films, A Comparison Between the Two Methods,"*J. Electroanal. Chem.*, vol. 186, pp. 191–199 (1985).

Seliskar et al., "Characterization of New Excimer Pumped UV Laser Dyes, 3. P–Quinqui–, Sexi–, Octi– and Deciphenyls," Laser Chem., vol. 13, pp. 19–28 (1993).

Semmelhack et al., "Reaction of Aryl and Vinyl Halides with Zerovalent Nickel–Preparative Aspects and the Synthesis of Alnusone," *J. Amer. Chem. Society*, vol. 103, No. 21, pp. 6460–6471 (1981).

Sheats et al., "Organic Electroluminescent Devices," *Science*, vol. 273, pp. 884–888 (Aug. 16, 1996).

Sorenson et al, *Preparative Methods of Polymer Chemistry*, Second Edidion, Interscience Publishers, Chapter 7 (1968).

Struklj et al., "Design and Application of Electron–Transporting Organic Materials," *Science*, vol. 267, pp. 1969–1972 (Mar. 31, 1995).

Tang et al., "Electroluminescence of doped organic thin films," *J. Appl. Phys.*, vol. 65, No. 9, pp. 3610–3616 (1989).

Tang et al., "Organic electroluminescent diodes," *Appl. Phys. Letters*, vol. 51, No. 12, pp. 913–915 (1987).

Uchida et al., "Visible and Blue Electroluminescent Diodes Utilizing Poly(3–Alkylthiopene)s and Poly(alkylfluorene)s," Synthetic Metals, 55–57, pp. 4168–4173 (1993).

Uchida et al., "Color–Variable Light–Emitting Diode Utilizing Conducting Polymer Containing Fluorescent Dye," *J. Appl. Phys.*, vol. 32, Part 2., No. 7A, pp. L921–L924 (1993).

Wallow et al., American Chemical Society *Polymer Preprint*, vol. 34(1), p. 1009 (1993).

Wallow et al., "Highly Efficient and Accelerated Suzuki Aryl Couplings Mediated by Phosphine–Free Palladium Sources," *Journal of Organic Chemistry*, vol. 59, pp. 5034–5037 (1994).

Wallow, Thomas, et al., "In Aqua Synthesis of Water–Soluble Poly(p–phenylene) Derivatives," *J. Am. Chem. Soc.*, vol. 115, pp. 7412–7414 (1991).

Weaver et al., "Recent progress in polymers for electroluminescence: microcavity devices and electron transport polymers," *Thin Solid Films*, vol. 273, pp. 39–47 (1996).

Woo et al., *Abstract of Meeting Papers*, Meeting of Material Research Society, "Highly Efficient LEDs Based on Fluorene Polymers," (Apr. 1998).

Wu, C.C. et al., "Poly (p–phenylene Vinylene)/Tris(8–hydroxy) Quinoline Aluminum Heterostructure Light Emitting Diode," *Appl. Phys. Lett.*, vol. 66, pp. 39–47 (1996).

Wunderly et al., "New Quench–resistant Fluors for Liquid Scintillation Counting," Int. J. Radiat. Appl. Instrum. Part A, Appl. Radiat. Isol., vol. 41, No. 9, pp. 809–815 (1990).

Yamamoto et al., "Polymer Light–Emitting Diodes with Single– and Double–Layer Structures Using Poly(2,3–diphenylquinoxaline–5,8–diyl)," *Japan Journal of Applied Physics*, vol. 33, pp. L250–L253 (Feb. 1994).

Yamamoto, "Electrically Conducting and Thermally Stable π–Conjugated Poly(Arylena)s Prepared by Organometallic Processes," *Progress in Polymer Science*, vol. 17, pp. 1153–1205 (1992).

Yang et al., "Novel Carbon Catalysis: Oxidation in Basic Solution," *Journal of Organic Chemistry*, vol. 58, p. 3754 (1958).

Yang et al., "Electron injection polymer for polymer light–emitting diodes," *Journal of Applied Physics*, vol. 77, No. 9, pp. 4807–4809 (1995).

Yang et al., "Efficient blue–green and white light–emitting electrochemical cells based on poly[9,9–bis(3,6–dioxaheptyl)–fluorene–2,7–diyl," *J. Appl. Phys.*, vol. 81, No. 7, pp. 3294–3298 (1997).

Yoshida et al., "Three–layered multicolor organic electroluminescent device," *Applied Physics Letters*, vol. 69, No. 6, pp. 734–736 (Aug. 5, 1996).

Zobel et al., "The Crystal Structures of Two Fluorene Derivatives," International Union of Crystallography, pp. 1170–1174 (1979).

SciFinder, Registry No. 95002–85–0, (Jan. 16, 2001).
SciFinder, Registry No. 109282–21–5, (Jan. 16, 2001).
SciFinder, Registry No. 109282–22–6, (Jan. 16, 2001).
SciFinder, Registry No. 135356–45–5, (Jan. 16, 2001).
SciFinder, Registry No. 90033–37–7, (Jan. 16, 2001).
SciFinder, Registry No. 94257–59–7, (Jan. 16, 2001).
SciFinder, Registry No. 144981–88–4, (Jan. 16, 2001).
SciFinder, Registry No. 145005–98–7, (Jan. 16, 2001).

SciFinder, Registry No. 117766–45–7, (Jan. 16, 2001).
SciFinder, Registry No. 56150–48–2, (Jan. 16, 2001).
SciFinder, Registry No. 56150–47–1, (Jan. 16, 2001).
SciFinder, Registry No. 1836–87–9, (Jan. 16, 2001).
SciFinder, Registry No. 80918–73–6, (Jan. 16, 2001).
SciFinder, Registry No. 65799–81–7, (Jan. 16, 2001).

SciFinder, Registry No. 153307–08–5, (Jan. 16, 2001).
SciFinder, Registry No. 153307–05–2, (Jan. 16, 2001).
SciFinder, Registry No. 133358–64–2, (Jan. 16, 2001).

* cited by examiner

FLUORENE-CONTAINING POLYMERS AND COMPOUNDS USEFUL IN THE PREPARATION THEREOF

CROSS-REFERENCE TO RELATED APPLICATIONS

This application is a continuation of prior application Ser. No. 09/661,237 (now granted as U.S. Pat. No. 6,512,083), filed Sep. 13, 2000, which is a continuation of application Ser. No. 08/861,469 (now granted as U.S. Pat. No. 6,169,163), filed May 21, 1997, which is a Continuation-in-Part of application Ser. No. 08/508,942 (now granted U.S. Pat. No. 5,708,130), filed Jul. 28, 1995 and of application Ser. No. 08/508,943 filed Jul. 28, 1995 (Abandoned).

BACKGROUND OF THE INVENTION

This invention relates to novel 2,7-dihalofluorenes which are substituted at the 9-position and methods for the preparation of such 9-substituted-2,7-dihalofluorenes. This invention further relates to oligomers and polymers of such fluorene compounds. This invention also relates to films and coatings prepared from such fluorenes, oligomers and polymers, processes for preparing such films and coatings, and light-emitting diodes comprised of one or more layers of polymer films at least one of which is derived from the oligomers and polymers of the invention.

Polymers and oligomers of fluorenes substituted by alkyl groups at the 9-carbon position have been reported by Fukuda et al. in *Japanese Journal of Applied Physics*, Vol. 28, pp. L1433–L1435 (1989). Such polymers are disclosed as useful as luminescent materials in the preparation of light-emitting diodes. These polymers were prepared by the Kovacic procedure wherein the appropriate fluorene monomers were treated for several days with a large excess of oxidizing metal salts such as ferric chloride. The structures are represented as poly(fluorene-2,7'-diyl)s. In a later article, Fukuda disclosed that the procedure used resulted in significant crosslinking and mislinking reactions during the polymerization. See Fukuda et al., *Journal of Polymer Science, Polymer Chemistry Edition*, Vol. 31, pp. 2465–2471 (1993). Brown et al., *Journal of Polymer Science Polymer Chemistry Edition*, Vol. 24, pp. 255–267 (1989) disclosed the presence of substantial chemical defects in the polymers formed by oxidative coupling polymerization of aromatic compounds under the reaction conditions of the Kovacic procedure, resulting in non-regioselective coupling and a significant number of polynuclear structures. Thus, it may be expected that oxidative coupling of fluorenes may frequently occur through other, non-desirable, positions, such as the 3,5'- and 3,6'-positions. In addition, it is possible that branching may occur as a result of attachment of more than two other fluorene molecules to a given fluorene molecule, thereby creating multifunctional sites for growth of branches. The presence of such by-products can result in low molecular weight oligomers and polymers with low degrees of polymerization. Such materials demonstrate a high polydispersity and low glass transition temperatures, properties that are detrimental to film quality. Indeed, Fukuda's polyfluorenes prepared by oxidative coupling have high polydispersity and low glass transition temperatures. Furthermore, the oxidative coupling process is very slow.

SUMMARY OF THE INVENTION

In one aspect, this invention is a compound of the formula:

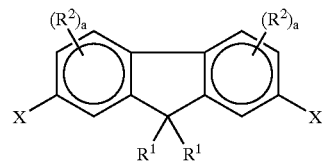

and compounds of the formulas:

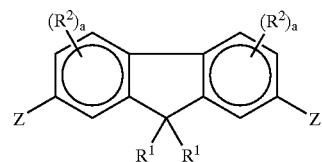

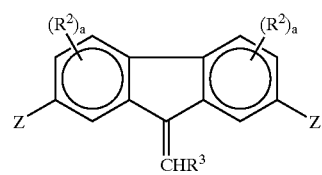

wherein $R^1$ is independently in each occurrence $C_{1-20}$ hydrocarbyl or $C_{1-20}$ hydrocarbyl containing one or more S, N, O, P or Si atoms, $C_{4-16}$ hydrocarbyl carbonyloxy, C4-16 aryl(trialkylsiloxy) or both $R^1$ may form with the 9-carbon on the fluorene ring a $C_{5-20}$ ring structure or a $C_{4-20}$ ring structure containing one or more heteroatoms of S, N or O;

$R^2$ is independently in each occurrence $C_{1-20}$ hydrocarbyl, $C_{1-20}$ hydrocarbyloxy, $C_{1-20}$ thioether, $C_{1-20}$ hydrocarbylcarbonyloxy or cyano;

$R^3$ is independently in each occurrence $C_{1-20}$ hydrocarbyl or $C_{1-20}$ hydrocarbyl substituted with di($C_{1-20}$ alkyl)amino, $C_{1-20}$ hydrocarbyloxy or $C_{1-20}$ hydrocarbyl or tri($C_{1-10}$ alkyl)siloxy;

a is independently in each occurrence 0 or 1;

X is independently in each occurrence a halogen moiety; and

Z is independently in each occurrence —B(OH)$_2$, —B(OR$^4$)$_2$ or

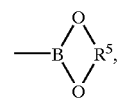

wherein $R^4$ is independently in each occurrence a $C_{1-10}$ alkyl group and $R^5$ is independently in each occurrence a $C_2$alkylene group.

In a second aspect, this invention is a composition containing polymers which have at least ten groups of the formula:

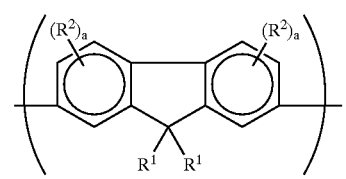

and a polydispersity of less than 5.

In a third aspect, this invention is a composition containing polymers, wherein an average of at least 10 percent by weight of each polymer is of the formula:

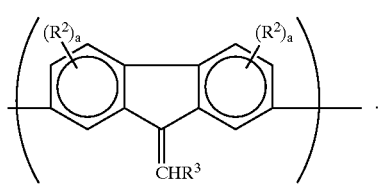

(V)

In a fourth aspect, this invention is a process for preparing polymers having at least three fluorene groups in it backbone, which comprises heating compounds of the formulas:

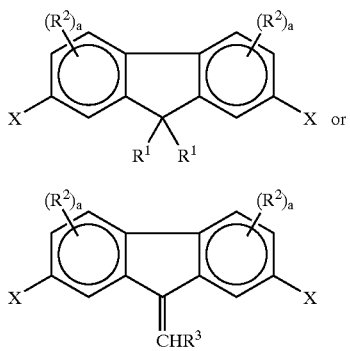

(I)

(VI)

or a mixture thereof, optionally in the presence of other compounds containing aryl halide groups, under reaction conditions sufficient to form a polymers having at least three groups of Formula (IV) or (V), or a combination thereof.

In a fifth aspect, this invention is a process for preparing polymers having at least three fluorene groups in its backbone, which comprises heating a mixture of compounds of the formulas:

X-A-X (VII) and Z-A-Z (VIII);

wherein A is independently in each occurrence a conjugated group, provided that A, in at least three occurrences, is a unit of Formula (IV) or (V); under reaction conditions sufficient to form the corresponding alternating copolymer.

In a sixth aspect, this invention is a film prepared from the polymers of this invention.

In a seventh aspect, this invention is a light-emitting diode comprised of one or more layers of polymer films, at least one of which is derived from the oligomers and polymers of the invention.

The compounds of the invention are useful in the preparation of the polymers of the second and third aspects of the invention. The polymers and oligomers of the invention do not contain a significant amount of misformed polynuclear structures or bonding through positions other than the 2- and 7'-positions, and they can be converted into films that are useful as light-emitting or carrier transport layers in light-emitting diodes. The polymers have good solubility characteristics and relatively high glass transition temperatures, which facilitates their fabrication into coatings and films that are relatively thin, thermally stable, and relatively free of defects. If the polymers contain end groups which are capable of being crosslinked, the crosslinking of such groups after the films or coating is formed increases the solvent resistance thereof, which is beneficial in applications wherein one or more solvent-based layers of material are deposited thereon. These and other advantages of the invention will be apparent from the description which follows.

DETAILED DESCRIPTION OF THE PREFERRED EMBODIMENTS

Preferred Substituents

"Hydrocarbyl" as used herein shall mean any organic moiety containing only hydrogen and carbon unless specified otherwise, and may include aromatic, aliphatic, cycloaliphatic and moieties containing two or more of aliphatic, cycloaliphatic and aromatic moieties.

$R^1$ is preferably $C_{1-12}$ alkyl, $C_{6-10}$ aryl or alkyl-substituted aryl, $C_{4-16}$ hydrocarbylcarbonyloxy, ($C_{9-16}$ aryl) trialkylsiloxy, a poly(alkyleneoxy) group having a terminal hydroxy, $C_{1-10}$ hydrocarbyloxy, or a group of the formula: $-(CH_2)_bCO_2R^6$, $-(CH_2)_bSO_3R^6$, $-(CH_2)_bN(R^1)_2$, $-(CH_2)_bN^+(R^1)_3$, or $-(CH_2)_b-CN$, wherein $R^6$ is a $C_{1-6}$ hydrocarbyl, H, $Li^+$, $Na^+$, or $K^+$. In the embodiment where the two $R^1$ form a ring structure with the 9-carbon atom of the fluorene ring, the ring structure formed is preferably a $C_{5-20}$ ring structure or a $C_{1-20}$ ring structure containing one or more heteroatoms of S, N or O; even more preferably a $C_{5-10}$ aliphatic ring or a $C_{4-10}$ aliphatic ring containing one or more of S or O; and most preferably a $C_{5-10}$ cycloalkyl or $C_{4-10}$ cycloalkyl containing oxygen.

The fluorene groups of the compounds of Formulas (I), (II), (III), and (IV) as well as the fluorene groups of other compounds used in the processes described herein can further be substituted at the 3-, 4-, 5- or 6-positions with substituents ($R^2$) which do not adversely affect the formation of oligomers of polymers therefrom, nor the subsequent processing of the oligomers or polymers for their intended uses. Preferably, $R^2$ is $C_{1-4}$ alkoxy, phenoxy, $C_{1-4}$ alkyl, phenyl or cyano. "a" is preferably 0. $R^3$ is preferably a $C_{1-20}$ straight- or branched-chain aliphatic, a $C_{1-20}$ straight- or branched-chain aliphatic containing one or more cycloaliphatic rings, $C_{6-20}$ aryl or $C_{7-20}$ alkyl-substituted aryl moiety, optionally substituted with a di($C_{1-20}$ alkyl) amino, $C_{1-20}$ hydrocarbyl, tri($C_{1-10}$ alkyl)siloxy or $C_{1-20}$ hydrocarbyloxy moiety. $R^3$ is more preferably a $C_{3-10}$ aliphatic, a $C_{3-10}$ aliphatic containing one or more cycloaliphatic moieties, phenyl or phenyl substituted with di($C_{1-12}$ alkyl)amino, $C_{1-10}$ alkoxy, $C_{6-10}$ aryloxy or alkyl-substituted aryloxy, $C_{1-10}$ alkyl or $C_{6-10}$ aryl or alkyl-substituted aryl or tri ($C_{1-4}$ alkyl)siloxy. Even more preferably, $R^3$ is phenyl or phenyl substituted with di($C_{1-6}$ alkyl)amino, $C_{1-10}$ alkoxy or $C_{1-10}$ alkyl.

In another embodiment, $R^3$ is preferably $C_{1-20}$ straight- or branched-chain aliphatic, $C_{3-20}$ straight- or branched-chain aliphatic containing a cycloaliphatic ring, $C_{6-20}$ aryl, or a $C_{7-20}$ alkyl-substituted aryl which may be further substituted with a di($C_{1-20}$ alkyl)amino, $C_{1-20}$ hydrocarbyloxy, tri($C_{1-10}$ alkyl)siloxy or $C_{1-20}$ hydrocarbyl. X is preferably chlorine or bromine; but is most preferably bromine. Z is preferably a cyclic boronate derived from ethylene glycol or propylene glycol.

Processes for Making Compounds of Formula (I)

The 2,7-dihalo-9,9-dihydrocarbyl-fluorenes may be prepared by reacting a 2,7-dihalofluorene with at least 2 moles of hydrocarbyl halide in the presence of a phase transfer catalyst and an alkali metal hydroxide. One embodiment of this process is described in Equation 1:

Equation 1

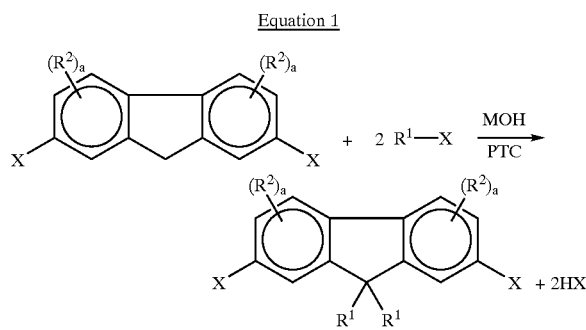

wherein $R^1$, $R^2$, X and a are as previously defined, M is an alkali metal and PTC is phase transfer catalyst.

Preferred hydrocarbyl halides are $C_{3-12}$ alkyl halides and $C_{6-10}$ alkaryl halides. More preferable are the $C_{3-12}$ alkyl halides.

The hydrocarbyl halide is contacted with the 2,7-dihalofluorene in a mole ratio such that a high yield of 2,7-dihalo-9,9-dihydrocarbylfluorene is prepared. Preferably, the mole ratio of hydrocarbyl halide to 2,7-dihalofluorene is 2:1 or greater, more preferably 2.2:1 or greater and even more preferably 3:1 or greater. Preferably, the mole ratio of hydrocarbyl halide to 2,7-dihalofluorene is 6:1 or less, more preferably 5:1 or less and most preferably 4:1 or less.

This process is preferably performed in the presence of an alkali metal hydroxide in a sufficient amount to facilitate the efficient reaction of the hydrocarbyl halide or hydrocarbyl dihalide with the 2,7-dihalofluorene. Preferably, 2 equivalents or greater of alkali metal hydroxide is used in relation to 2,7-dihalofluorene and, more preferably 3 equivalents or greater of alkali metal hydroxide. Preferably, 20 equivalents or less of alkali metal hydroxide per equivalent of 2,7-dihalofluorene are used, more preferably 8 equivalents or less and most preferably 4 equivalents or less. Preferred alkali metal hydroxides useful are sodium hydroxide and potassium hydroxide, with sodium hydroxide being most preferred.

This process is an interfacial process using phase transfer catalysts. Any phase transfer catalyst known to those skilled in the art may be used. A sufficient amount of such phase transfer catalyst to facilitate the reaction of the hydrocarbyl halide or hydrocarbyl dihalide with the 2,7-dihalofluorene in a reasonably efficient manner is used. Preferable phase transfer catalysts include quaternary ammonium salts, quaternary phosphonium salts, polyethylene glycols and crown ethers. More preferred phase transfer catalysts are the quaternary ammonium salts. Examples of preferred quaternary ammonium salts useful as phase transfer catalysts include benzyltrimethylammonium chloride, benzyltriethylammonium chloride and tetrabutylammonium bromide. The phase transfer catalysts preferably are used in an amount of 0.0001 mole or greater of catalyst per mole of 2,7-dihalofluorene, more preferably 0.001 mole or greater and even more preferably 0.01 mole or greater. Preferably, 0.2 mole or less of catalyst per mole of 2,7-dihalofluorene is used, more preferably 0.15 mole or less and even more preferably 0.02 mole or less.

The 2,7-dihalo-9-cyclohydrocarbylfluorene (compounds of Formula (I) wherein both $R^1$ form with the 9-carbon on the fluorene ring a $C_{5-20}$ ring structure or a $C_{4-20}$ ring structure containing one or more heteroatoms of S, N or O) may be prepared by contacting 1 mole of 2,7-dihalofluorene with 1 mole of hydrocarbyl dihalide in a manner similar to that described for the preparation of compound I.

This process is described in Equation 2:

Equation 2

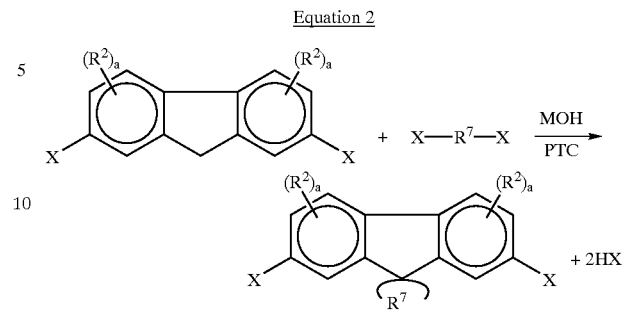

wherein $R^2$, X and a are as previously defined. $R^7$ is a $C_{4-20}$ straight- or branched-chain aliphatic divalent moiety or $C_{3-20}$ straight- or branched-chain aliphatic divalent moiety containing one or more heteroatoms comprising S, N or O.

Preferred hydrocarbyl dihalides are $C_{4-20}$ straight- or branched-chain aliphatic dihalides or $C_{3-20}$ straight- or branched-chain aliphatic dihalides containing one or more heteroatoms comprising S, N or O. More preferred hydrocarbyl dihalides are $C_{4-10}$ aliphatic dihalides or $C_{3-10}$ aliphatic dihalides containing one or more of S or O. Even more preferred hydrocarbyl dihalides are $C_{3-10}$ alkyl dihalides and $C_{3-10}$ alkyl ether dihalides ($C_{3-10}$ alkyl dihalides containing an oxygen). $R^7$ is more preferably a $C_{4-10}$ aliphatic divalent moiety or a $C_{3-10}$ aliphatic divalent moiety containing one or more of S or O. $R^7$ is even more preferably a divalent $C_{4-10}$ alkyl or $C_{3-10}$ alkyl ether ($C_{3-10}$ alkyl containing an oxygen atom).

The 2,7-dihalofluorene substituted at the C-9 position with $-(CH_2)_2-CO_2R^6$ and $-CH_2CH(CH_3)CO_2R^8$ (wherein $R^8$ is a $C_{1-10}$ alkyl group) may be prepared by base catalyzed addition of 2,7-dihalofluorene to alkyl acrylates and alkyl methacrylates, using the process conditions described in U.S. Pat. No. 3,641,115.

The 2,7-dihalo-9,9 di-$C_{9-16}$ aryl(trialkylsiloxy)-substituted fluorenes may be prepared by the following process. 2,7-Dihalofluorenone is reacted with phenol in a mixture of methanesulfonic acid and 3-mercaptopropionic acid to provide 2,7-dihalo-9,9-bis(4-hydroxyphenyl) fluorene which is then treated with a trialkylsilyl chloride in the presence of a base to yield the 2,7-dihalo-9,9-bis(4-trialkylsiloxyphenyl) fluorene. 2,7-Dihalofluorenone can be prepared by the oxidation of 2,7-dihalofluorene with oxygen in the presence of a base, such as potassium t-butoxide, in t-butyl alcohol. The reaction conditions for this process are disclosed by Yang in "Novel Carbon Catalysts: Oxidation in Basis Solution," *J. Organic Chemistry*, Vol. 58, p. 3754 (1958). Alternatively, 2,7-dihalofluorene can be oxidized to 2,7-dihalofluorenone by contacting it with chromium oxide ($CrO_3$) in acetic acid according to the process disclosed by Hodgkinson et al. in *J. Chem. Soc.*, Vol. 43, pp. 163–172 (1983). The 2,7-dihalofluorenone is contacted with 3 to 10 equivalents of phenol in the presence of from 30 to 100 percent by weight of methanesulfonic acid and from 2 to 10 percent by weight of mercaptopropionic acid. The reaction is preferably performed at a temperature of from 20° C. to 50° C. The 4-hydroxyphenyldihalofluorene is recovered by conventional techniques before reaction with the trialkylsilyl chloride.

The 2,7-dihalo-9,9-bis(4-hydroxyphenyl) fluorene is contacted with from 2.2 to 3.0 equivalents of trialkylsilyl chloride in the presence of from 3.0 to 6.0 equivalents of base. The reaction is preferably performed at a temperature of from 20° C. to 40° C. The reaction is preferably performed in a solvent of dimethylformamide and dimethylacetamide. Imidazole is the preferred base. The 2,7-dihalo-9,9-bis(4-trialkylsiloxy)fluorene can be recovered by conventional techniques.

The 2,7-dihalo-9-substituted fluorenes may be further substituted on the 3-, 4-, 5- and/or 6-position ($R^2$ groups) by any suitable synthesis technique. Preferably, the 3-, 4-, 5- and/or 6-positions are substituted prior to substitution at the 9-position. In many instances, the reaction sequence to place substituents at the 3-, 4-, 5- and/or 6-position may result in unwanted substitution with the substituents at the 9-position if the substitution is performed after the 9-position substitution.

Process for Making Compounds of Formulas (II) and (III)

The boron-containing compounds of Formulas (II) and (III) may be prepared by any suitable method. An example of reaction conditions for preparing boron-containing compounds is described in Remmers et al., *Macromolecular Rapid Communications*, Vol. 17, 239–253 (1996). Compounds of Formulas (I) and (VI) are converted to the corresponding dilithio derivative by reaction with two equivalents of butyllithium. Reaction of the dilithio derivative with a trialkylborate followed by hydrolysis yields the diboronic acid (Formulas (II) and (III), Z=B(OH)$_2$). Esterification of the diboronic acid with an alkylenediol, such as ethylene glycol, gives the di(cyclic)boronate.

Compounds corresponding to Formula (VI) may be prepared by the reaction of a hydrocarbylaldehyde or a substituted hydrocarbylaldehyde with a dihalofluorene compound in the presence of base as a catalyst. Preferably, the aldehyde corresponds to the formula —$R^3$CHO; wherein $R^3$ is as defined previously. In a more preferred embodiment, the hydrocarbyl moiety is a phenyl, a substituted phenyl, a $C_{3-10}$ aliphatic moiety or a $C_{5-10}$ cycloaliphatic moiety and the aldehyde is benzaldehyde, substituted benzaldehyde, $C_{3-10}$ aliphatic aldehyde or $C_{5-10}$ cycloaliphatic aldehyde. This reaction is illustrated by Equation 3:

Equation 3

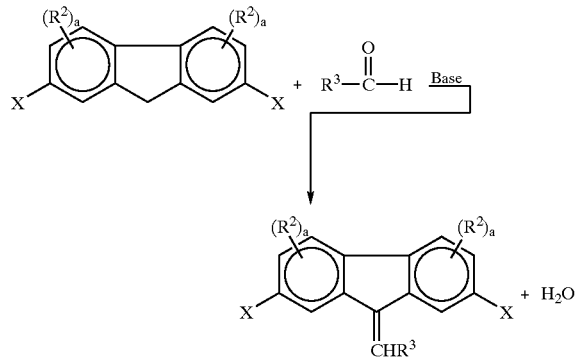

wherein X, $R^2$, $R^3$ and a are as previously defined.

The 2,7-dihalofluorene is reacted with a sufficient amount of hydrocarbylaldehyde to prepare the hydrocarbylidene-substituted 2,7-dihalofluorenes in high yield. Preferably, the mole ratio of hydrocarbylaldehyde to 2,7-dihalofluorene is 1.0 or greater, more preferably 1.5 or greater and even more preferably 2 or greater. Preferably, the mole ratio of hydrocarbylaldehyde to 2,7-dihalofluorene is 6 or less, more preferably 3 or less and most preferably 2 or less.

In one preferred embodiment, the 2,7-dihalo-9-hydrocarbylidenylfluorene is a 2,7-dihalo-9-benzylidenylfluorene corresponds to Formula (IX):

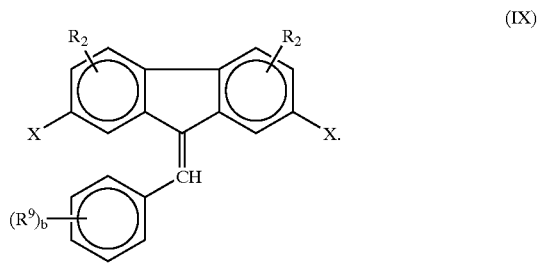

"Hydrocarbylidene" as used herein shall mean a hydrocarbyl moiety bound by a double bond to the 9-position of the fluorene ring. $R^9$ is independently in each occurrence di($C_{1-20}$ alkyl)amino, $C_{1-20}$ hydrocarbyloxy, tri($C_{1-0}$ alkyl)siloxy or $C_{1-20}$ hydrocarbyl. b is independently in each occurrence a number of from 0 to 3, is preferably no greater than 2, and is most preferably no greater than 1. $R^9$ is preferably di($C_{1-12}$ alkyl)amino, $C_{1-10}$ alkoxy, $C_{6-10}$ aryloxy or alkyl-substituted aryloxy, tri($C_{1-4}$ alkyl)siloxy, $C_{1-10}$ alkyl, or $C_{6-10}$ aryl or alkyl-substituted aryl. Even more preferably, $R^9$ is di($C_{1-6}$ alkyl)amino, $C_{1-10}$ alkoxy or $C_{1-10}$ alkyl. In another embodiment, $R^9$ preferably is $C_{1-10}$ alkyl $C_{6-10}$ aryl or $C_{7-10}$ alkyl aryl and more preferably $C_{1-10}$ alkyl. Preferably, b is 0 to 2, and most preferably b is 1.

Description of Polymers

Preferably, the oligomers and polymers of the invention comprise at least 20 percent by weight of the groups of Formulas (IV) and (V) or a combination thereof, more preferably at least 25 percent by weight, and most preferably at least 50 percent by weight.

In a preferred embodiment, the fluorene oligomers or polymers containing groups of Formulas (IV) and (V) correspond to Formula (X):

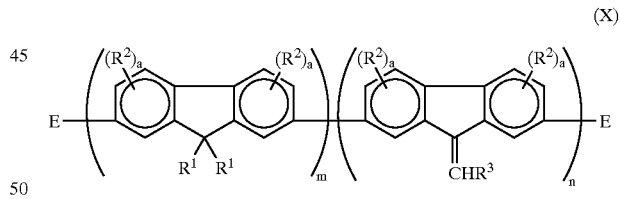

wherein m+n is 3 or greater and n/(m+n) is from zero to 1, and substantially all of the monomer units are connected to end moieties or other monomer units through the 2- and 7-carbon atoms. E is hydrogen or an aryl moiety which may optionally be substituted with a reactive group capable of undergoing chain extension or crosslinking, or a trialkylsiloxy group. As used herein, a reactive group capable of undergoing chain extension or crosslinking refers to any group which is capable of reacting with another of the same group or another group so as to form a link to prepare oligomers or polymers. Preferably, such reactive group is a hydroxy, glycidyl ether, acrylate ester, methacrylate ester, ethenyl, ethynyl, maleimide, nadimide, trifluorovinyl ether moiety or a cyclobutene moiety fused to the aromatic ring of E.

In another embodiment, the fluorene oligomers or polymers correspond to Formula (XI):

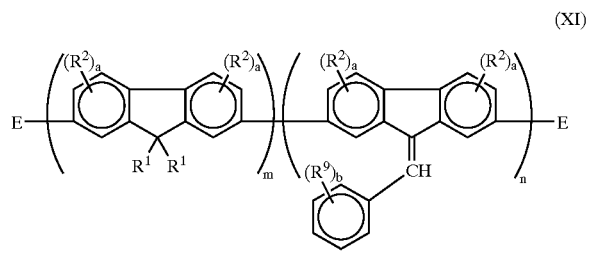

(XI)

wherein $R^1$, $R^2$, $R^9$, E, a, m and n are as defined above.

As used herein the term "fluorene oligomers and polymers" refers to oligomers and polymers having groups of Formula (IV) and (V) or a combination thereof.

The fluorene oligomers or polymers of the invention demonstrate strong photo-luminescence in dilute solutions or in the solid state. When such materials are exposed to a light of a wavelength of 300 to 700 nanometers, the materials emit light of wavelengths in the region of 400 to 800 nanometers. More preferably, such materials absorb light of wavelengths of from 350 to 400 nanometers and emit light of wavelengths in the region of 400 to 650 nanometers. The fluorene oligomers or polymers of the invention are readily soluble in common organic solvents. They are processible into thin films or coatings by conventional techniques. Generally, the fluorene oligomers and polymers of this invention are liquid crystalline in nature.

The fluorene oligomers or polymers of this invention preferably have a weight average molecular weight of 1000 Daltons or greater, more preferably 5000 Daltons or greater, even more preferably 10,000 Daltons or greater, even more preferably 15,000 Daltons or greater and most preferably 20,000 Daltons or greater; preferably 1,000,000 Daltons or less, more preferably 500,000 Daltons or less and most preferably 200,000 Daltons or less. Molecular weights are determined according to gel permeation chromatography using polystyrene standards. The degree of polymerization of the polymers of the invention (m+n) is preferably at least 30.

Preferably, the 9-substituted fluorene oligomers or polymers demonstrate a polydispersity (Mw/Mn) of 5 or less, more preferably 4 or less, even more preferably 3 or less, even more preferably 2.5 or less and most preferably 2.0 or less.

Processes for Preparing Polymers

The polymers containing groups of Formulas (IV) and (V) may be prepared by any suitable process, but are preferably prepared by the processes described below. The condensation reaction of an aromatic boronate and a bromide, commonly referred to as the "Suzuki reaction", is tolerant of the presence of a variety of organic functional groups and as reported by N. Miyaua and A. Suzuki in *Chemical Reviews*, Vol. 95, pp. 457–2483 (1995). This reaction can be applied to preparing high molecular weight polymers and copolymers. To prepare polymers corresponding to Formula (V) (E=H, Br, or aromatic group), a dibromide corresponding to Formula (I), Formula (VI), or a mixture thereof is reacted with an equimolar amount of diboronic acid or diboronate corresponding to Formulas (II), (III), or a mixture thereof under the catalytic action of Pd and triphenylphosphine. The reaction is typically conducted at about 70° C. to 120° C. in an aromatic hydrocarbon solvent such as toluene. Other solvents such as dimethylformamide and tetrahydrofuran can also be used alone, or in mixtures with, an aromatic hydrocarbon. An aqueous base, preferably sodium carbonate or bicarbonate, is used as the HBr scavenger. Depending on the reactivities of the reactants, a polymerization reaction may take 2 to 100 hours. Other variations of reaction conditions are given by T. I. Wallow and B. M. Novak in *Journal of Organic Chemistry*, Vol. 59, pp. 5034–5037 (1994); and M. Remmers, M. Schulze, and G. Wegner in *Macromolecular Rapid Communications*, Vol. 17, pp. 239–252 (1996). An alternating copolymer results when a dibromide corresponding to a dibromofluorene represented by Formula (I) is reacted with a diboronate corresponding to a fluorene diboronate represented by Formula (III). If desired, a monofunctional aryl halide or aryl boronate may be used as a chain-terminator in such reactions, which will result in the formation of a terminal aryl group.

Polymerization processes involving only dihalofunctional reactants may be carried out using nickel coupling reactions. One such coupling reaction was described by Colon et al. in *Journal of Polymer Science*, Part A, Polymer Chemistry Edition, Vol. 28, p. 367 (1990), incorporated herein by reference, and by Colon et al. in *Journal of Organic Chemistry*, Vol. 51, p. 2627 (1986). The reaction is typically conducted in a polar aprotic solvent (e.g., dimethylacetamide) with a catalytic amount of nickel salt, a substantial amount of triphenylphosphine and a large excess of zinc dust. A variant of this process is described by Ioyda et al. in *Bulletin of the Chemical Society of Japan*, Vol. 63, p. 80 (1990) wherein an organo-soluble iodide was used as an accelerator. Another nickel-coupling reaction was disclosed by Yamamoto in *Progress in Polymer Science*, Vol. 17, p. 1153 (1992) wherein a mixture of dihaloaromatic compounds were treated with an excess amount of nickel (1,5-cyclooctadiene) complex in an inert solvent. All nickel-coupling reactions when applied to reactant mixtures of two or more aromatic dihalides yield essentially random copolymers. Such polymerization reactions may be terminated by the addition of small amounts of water to the polymerization reaction mixture, which will replace the terminal halogen groups with hydrogen groups. Alternatively, a monofunctional aryl halide may be used as a chain-terminator in such reactions, which will result in the formation of a terminal aryl group.

Copolymers Containing Other Conjugated Groups

In one embodiment, the polymers of the invention contain conjugated groups other than the fluorene groups described above. "Conjugated groups" refer to moieties containing double bonds, triple bonds and/or aromatic rings. The incorporation of such groups into the polymer may be used to modify the light absorption, ionization potential, and/or electronic properties of the polymer which would otherwise be primarily comprised of 9,9-disubstituted fluorene groups. Such polymers may be prepared using the methods described above incorporating at least one conjugated compound different from the fluorene compounds described above. Such conjugated compounds, hereinafter referred to as "comonomers", have functional groups which permit them to copolymerize with the fluorene compounds. For example, dihalo-functional comonomers are preferably used in conjunction with dihalo-functional fluorene compounds in nickel-coupling polymerization reactions; dihalo-functional comonomers are preferably used in conjunction with fluorene-diboronic acids or fluorene-diboronates; and conjugated comonomers bearing diboronic acid or diboronate functionalities are preferably used in conjunction with 2,7-dibromofluorenes. For the purpose of preparing high molecular weight polymers of the invention, more than one diboronic acid/diboronate and more than one dibromide may be used in a Suzuki polymerization reaction so long as the total molar amount of diboronic acids/diboronates is essentially equivalent to the total amount of dibromides.

Nickel-coupling polymerizations yield essentially random copolymers comprising fluorene group-containing units and units derived from other conjugated monomers, while Suzuki polymerizations yield alternating copolymers.

It is possible to control the sequencing of the monomeric units in the resulting copolymer by controlling the order and composition of monomer feeds in the Suzuki reaction. For instance, a high molecular weight copolymer comprising mainly large blocks of fluorene homopolymers connected to short blocks of alternating fluorene-comonomer oligomers may be made by first introducing into the reaction reactants in the appropriate ratio to make the alternating fluorene-comonomer oligomers followed by the remainder of fluorene monomers so long as there is an overall balance of boronic and bromo groups.

Examples of conjugated comonomers include stilbene, tolan, $C_6$–$C_{20}$ mononuclear/polynuclear aromatic hydrocarbons, and $C_2$–$C_{10}$ mononuclear/polynuclear heterocycles; and tertiary aromatic amines.

Examples of mononuclear/polynuclear aromatic hydrocarbons include benzene, naphthalene, acenaphthene, phenanthrene, anthracene, fluoranthene, pyrene, rubrene, and chrysene. Examples of mononuclear/polynuclear heterocycles include 5-member heterocycles such as furan, thiophene, pyrrole, oxazole, isooxazole, thiazole, isothiazole, imidazole, oxadiazoles, thiadiazole, and pyrazoles; 6-member heterocycles such as pyridine, pyridazine, pyrimidine, pyrazine, triazines, and tetrazenes; benzo-fused ring systems such as benzoxazole, benzothiazole, benzimidazole, quinoline, isoquinoline, cinnoline, quinazoline, quinoxaline, phthalazine, benzothiadiazole, and benzotriazines; and polynuclear condensed ring systems such as phenazine, phenanthridine, acridine, carbazole, and diphenylene oxide. Examples of tertiary aromatic amines include triphenyl amine, alkyldiaryl amines, N,N,N',N'-tetraphenylbenzidine, N,N,N',N'-tetraphenyl-1,4-phenylenediamine. In general, conjugated compounds containing up to 30 carbons are useful for the present purpose. They may be substituted optionally with one or more substituents that are not deleterious to the photoluminescent properties of the polymer compositions. Examples of substituents include $C_1$–$C_{20}$ hydrocarbyl radicals, $C_1$–$C_{20}$ (thio) alkoxy radicals, $C_1$–$C_{20}$ (thio)aryloxy radicals, cyano, fluoro, chloro, $C_1$–$C_{20}$ alkoxycarbonyl, $C_1$–$C_{20}$ aryoxylcarbonyl, $C_1$–$C_{20}$ carboxyl and alkyl(aryl)sulfonyl radicals. Substituents which are known photoluminescent quenchers, such as arylcarbonyl and nitro, are undesirable.

Conjugated monomeric units of more complex structures, as exemplified by Structures (1)–(5), may also be used.

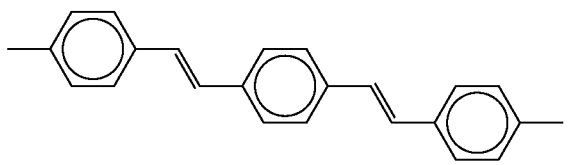

(1)

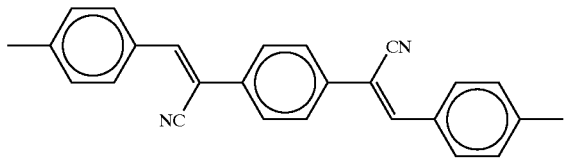

(2)

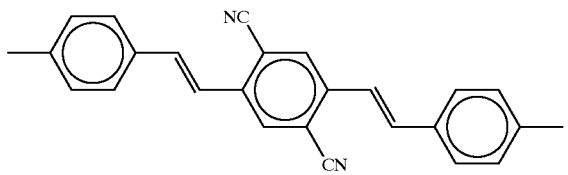

(3)

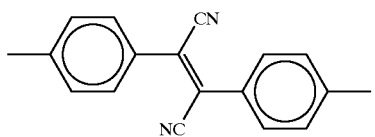

(4)

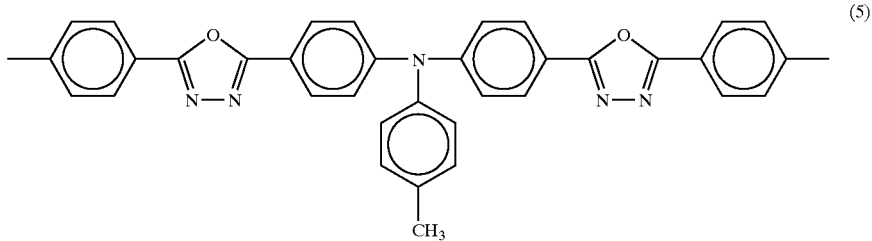

(5)

Crosslinkable Derivatives

The fluorene oligomers or polymers of the invention, where E are reactive groups as defined above, are capable of crosslinking to form solvent resistant, heat-resistant films at 100° C. or more, more preferably at 150° C. or more. Preferably, such crosslinking occurs at 350° C. or less, more preferably 300° C. or less and most preferably 250° C. or less. The crosslinkable polymers of the invention are stable at 100° C. or more and more preferably 150° C. or more. "Stable" as used herein means that such oligomers do not undergo crosslinking or polymerization reactions at or below the stated temperatures. If a crosslinkable material is desired, E in Formulas (X) and (XI) is preferably a vinylphenyl, an ethynylphenyl, or 4-(or 3-)benzocyclobutenyl radical. In another embodiment, E is selected from a group of phenolic derivatives of the formula —$C_6H_4$—O—Y wherein:

Y=—H, —CN,

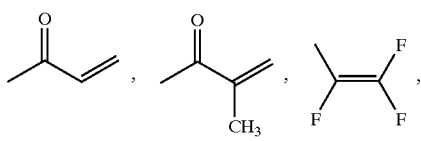

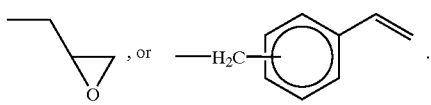

In one preferred embodiment, the invention comprises 2,7-aryl-9,9-dihydrocarbyl- or cyclohydrocarbylfluorene oligomers and polymers which correspond to Formula (XII):

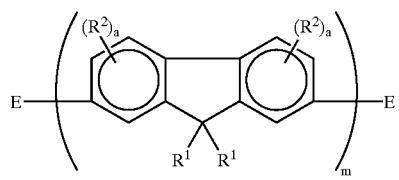

wherein E, $R^1$, $R^2$, and a are as described above, and m is at least 1.

In another embodiment, the invention comprises 2,7-aryl-9-hydrocarbylidenyl-fluorenes and 9-hydrocarbylidenyl-fluorene oligomers and polymers thereof which preferably correspond to Formula (XIII):

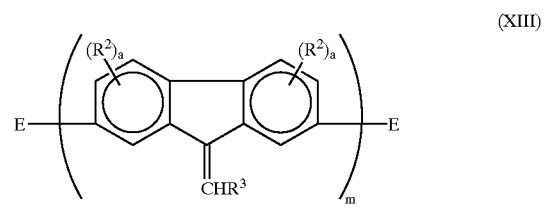

wherein E, $R^2$, $R^3$, a and m are as described above.

In one preferred embodiment, the 2,7-aryl-9-hydrocarbylidenylfluorene oligomers and polymers are 2,7-aryl-9-benzylidenylfluoreneoligomers and polymers which correspond to Formula (XIV):

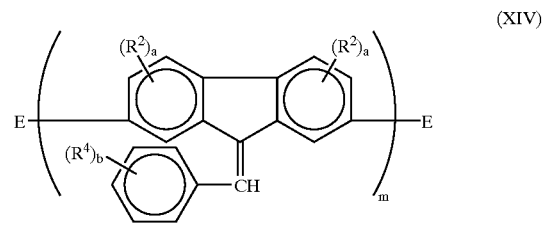

wherein E, $R^2$, $R^9$, a, b and m are as described above.

The crosslinkable materials of Formulas (X) to (XIV) are prepared by contacting a mixture of monomers selected from those represented by Formulas (I) and (VI), and optionally one or more conjugated comonomers, an end-capping agent E-X (E is as defined above and X is either Cl or Br) under the condition in which the resulting oligomers and polymers are substantially capped by the reactive group E. The reactions useful for this purpose are the nickel-coupling and Suzuki reactions described above. The average degree of polymerization is controlled by the mole ratio of monomers to end-capping agent. A mole ratio of 10:2 (monomers:end-capping agent) will provide a crosslinkable material with an average degree of polymerization of 10; similarly a mole ratio of 6:2 will provide crosslinkable material with an average degree of polymerization of 6.

In the embodiment wherein E is vinylphenyl, ethynylphenyl or 4-benzocyclo-butenyl, the end-capping agents are bromostyrene, ethynylphenyl bromide, and 4-bromobenzocyclobutene respectively. In the embodiment where E is a phenolic derivative, the end-capping agent is 3-(or 4-)bromophenyl trialkylsilylether, as illustrated by Equation 4, wherein $R^{10}$ is a $C_{1-20}$ alkyl moiety, preferably a $C_{1-4}$ alkyl moiety. The trialkylsilyl moieties may be converted to hydroxy moieties by contact with concentrated acid, such as hydrochloric acid, in an organic solvent as illustrated by Equation 5.

The hydroxy moieties of the 2,7'-aryl substituents may be converted to cyanate moieties by well-known cyanation reactions. See, for example, U.S. Pat. No. 4,478,270; Martin, *Organic Synthesis*, Vol. 61, p. 35; and *Handbook of Preparative Inorganic Chemistry*, pg. 1662 (1963), Academic Press, New York. This reaction sequence is illustrated by Equation 6.

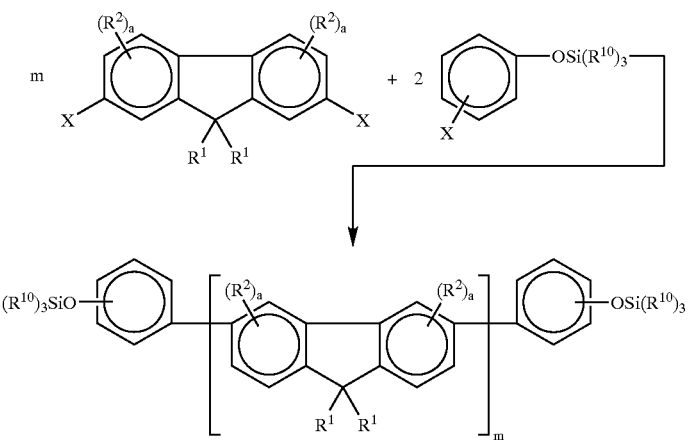

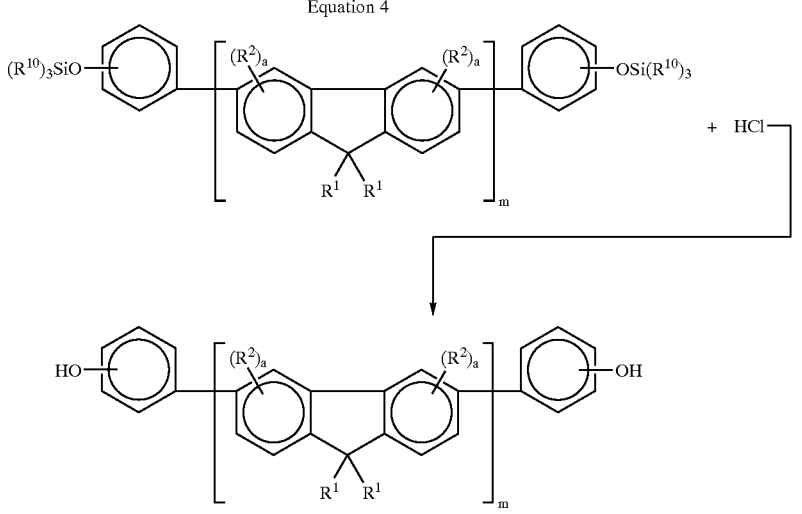

Equation 4

Equation 5

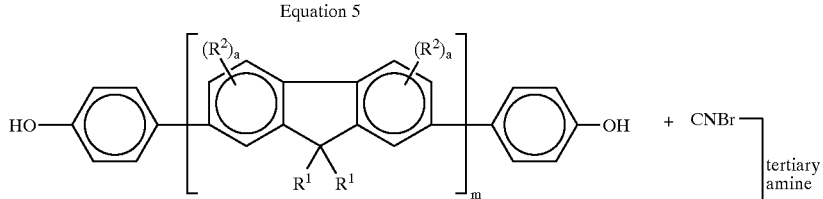

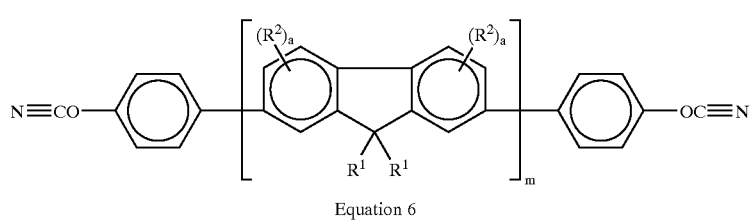

Equation 6

In one preferred embodiment, the 2,7'-hydroxyaryl-9-substituted fluorene oligomer or polymer is contacted with a cyanogen halide dissolved in a chlorinated hydrocarbon or a secondary or tertiary alcohol, in the presence of a tertiary amine at a temperature of 0° C. or less, under conditions such that the hydroxy moieties are replaced with cyanate moieties. Preferably, the contacting occurs in the presence of a dilute base such as alkali or alkaline metal hydroxides, alkali or alkaline metal carbonates, or alkali or alkaline metal bicarbonates or tertiary amines. Preferred bases are the tertiary amines with the aliphatic tertiary amines being most preferred. This process is preferably run at a temperature of 0° C. or lower with temperatures of −10° C. or lower being most preferred. It is preferable to perform such process under an inert gas atmosphere. The cyanated-2,7'-aryl-9-substituted fluorene oligomers or polymers may be recovered by washing the reaction solution with a dilute base to remove excess cyanogen chloride. The reaction solution is thereafter washed with water so as to remove any salt prepared from the hydrochloride by-product and base. The reaction solution is then contacted with the dilute acid to neutralize any base which may be present. Thereafter, the reaction solution is contacted with water again so as to remove any other impurities and the cyanated 2,7'-aryl-9-substituted fluorene oligomers or polymers are recovered by drying the solution with the use of a desiccant.

The reactions illustrated by Equations 4, 5 and 6 can also be performed starting with 9-hydrocarbylidenyl-2,7-dihalofluorene. In another embodiment, the hydroxy moieties of the 2,7'-dihydroxyaryl-9-substituted fluorene oligomer or polymer may be converted to glycidyl ether moieties by processes well known in the art. Such glycidyl ethers are preferably prepared by contacting the 2,7'-dihydroxyaryl-9-substituted fluorene oligomer or polymer with epihalohydrin under conditions to form aryl moieties with chlorohydrin groups at their termini. The chlorohydrin groups are dehydrohalogenated to form an epoxy or glycidyl ring by contacting them with sodium hydroxide. Such process is described in Handbook of Epoxy Resins, Lee and Neville (1967). This process is illustrated by Equation 7.

percent to 99 percent of the blend is composed of one or more polymeric materials selected from among chain growth polymers such as polystyrene, polybutadiene, poly (methyl methacrylate), and poly(ethylene oxide); step-growth polymers such as phenoxy resins, polycarbonates, polyamides, polyesters, polyurethanes, and polyimides; and crosslinked polymers such as crosslinked epoxy resins, crosslinked phenolic resins, crosslinked acrylate resins, and crosslinked urethane resins. Examples of these polymers may be found in *Preparative Methods of Polymer Chemistry*, W. R. Sorenson and T. W. Campbell, Second Edition, Interscience Publishers (1968). Also may be used in the blends are conjugated polymers such as poly(phenylene vinylene), substituted poly(phenylene vinylene)s, substituted polyphenylenes and polythiophenes. Examples of these conjugated polymers are given by Greenham and Friend in *Solid State Physics*, Vol. 49, pp. 1–149 (1995). The most preferred blend composition is composed of at least 51 percent of a conjugated polymer and at most 49 percent of a fluorene-containing polymer of this invention with the provision that the band-gap of the fluorene-containing polymer is narrower than the band-gap of the conjugated polymer. These most preferred compositions have high photoluminescent and electroluminescent efficiency.

Polymer Applications

Another aspect of the invention is the films formed from the oligomers and polymers of the invention. Such films can be used in polymeric light-emitting diodes. Preferably, such films are used as emitting layers or charge carrier transport layers. These oligomers and polymers may also be used as

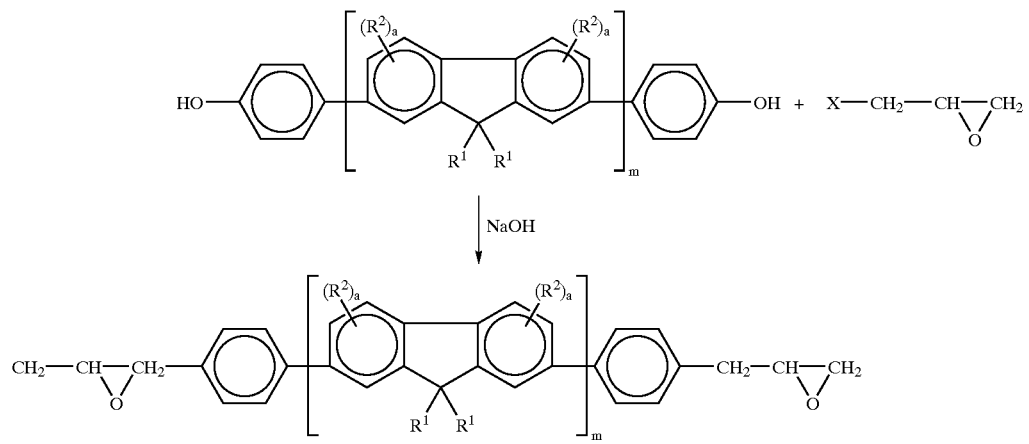

Equation 7

Polymer Blends

Another aspect of this invention is a blend of at least two light-emitting polymers, wherein the maximum emission wavelength of the first polymer is within 25 nm of the maximum absorption wavelength of the second polymer, and wherein the second polymer is present in an amount, based on the weight of the first polymer, of 0.1 to 49 percent. Preferably, the first light-emitting polymer is a polymer containing groups of Formula (IV), (V), or a mixture thereof. Preferably, the second polymer is an alternating copolymer having groups of Formula (IV), (V), and a mixture thereof, and groups derived from a different conjugated monomer.

Another aspect of this invention is related to polymer blends containing 1 to 99 percent of at least one fluorene-containing polymer of this invention. The remainder 1 protective coatings for electronic devices and as fluorescent coatings. The thickness of the coating or film is dependent upon the ultimate use. Generally, such thickness can be from 0.01 to 200 microns. In that embodiment wherein the coating is used as a fluorescent coating, the coating or film thickness is from 50 to 200 microns. In that embodiment where the coatings are used as electronic protective layers, the thickness of the coating can be from 5 to 20 microns. In that embodiment where the coatings are used in a polymeric light-emitting diode, the thickness of the layer formed is 0.05 to 2 microns. The oligomers or polymers of the invention form good pinhole- and defect-free films. Such films can be prepared by means well known in the art including spin-coating, spray-coating, dip-coating and roller-coating. Such coatings are prepared by a process comprising applying a composition to a substrate and exposing the applied composition to conditions such that a film is formed. The conditions which form a film depend upon the application technique and the reactive end groups of the aryl moiety. In a preferred embodiment, the composition applied to the substrate comprises the 2,7-diaryl-9-substituted fluorene oligomers or polymers dissolved in a common organic solvent. Preferably, the solution contains from 0.1 to 10 weight percent of the oligomers or polymers. For thin coatings, it is preferred that the composition contains from 0.5 to 5.0 percent by weight of the oligomers or polymers. This composition is then applied to the appropriate substrate by the desired method and the solvent is allowed to evaporate. Residual solvent may be removed by vacuum and/or by heat. If the solvent is low boiling, then low solution concentrations, for example, 0.1 to 2 percent, are desired. If the solvent is high boiling, then high concentrations, for example, 3 to 10 percent, are desired. After removal of the solvent, the coating is then exposed to the necessary conditions to cure the film, if needed, to prepare a film having high solvent and heat resistance. The films are preferably substantially uniform in thickness and substantially free of pinholes. Preferably, the films are cured when exposed to temperatures of 100° C. or greater, more preferably 150° C. or greater and most preferably 200° C. or greater. Preferably, the films cure at a temperature of 300° C. or less.

In the preparation of the films, the composition may further comprise a catalyst suitable to facilitate or initiate the curing of the films. Such catalysts are well known in the art, for instance, for materials having ethylenic unsaturation, a free radical catalyst may be used. For aryl moieties with glycidyl ethers as end-groups, ureas or imidazoles may be used. In the preparation of films from fluorenes with glycidyl ether aryl-terminal moieties, such materials may be reacted with commonly known curing agents which facilitate crosslinking. Among preferred curing agents are tetrahydrophthalic anhydride, nadic anhydride and maleic anhydride.

In another embodiment, the 2,7-diaryl-9-substituted fluorene oligomers or polymers may be partially cured. This is known as B-staging. In such embodiment, the fluorenes and their oligomers or polymers thereof are exposed to conditions such that a portion of the reactive materials cure and a portion of the reactive materials do not cure. This is commonly used to improve the handleability of such a resin and can facilitate the preparation of the films. Such B-staged material can thereafter be used to prepare coatings by the means disclosed above. Preferably, 10 mole percent or greater of the reactive moieties are reacted. Preferably, 50 mole percent or less of the reactive moieties are reacted.

Yet another aspect of the invention relates to organic electroluminescent (EL) devices comprising a film of the polymers of this invention. An organic El device typically consists of an organic film sandwiched between an anode and a cathode such that when a positive bias is applied to the device, holes are injected into the organic film from the anode, and electrons are injected into the organic film from the cathode. The combination of a hole and an electron may give rise to an exciton which may undergo radiative decay to the ground state by liberating a photon. In practice the anode is commonly an mixed oxide of tin and indium for its conductivity and transparency. The mixed oxide (ITO) is deposited on a transparent substrate such as glass or plastic so that the light emitted by the organic film may be observed. The organic film may be the composite of several individual layers each designed for a distinct function. Since holes are injected from the anode, the layer next to the anode needs to have the functionality of transporting holes. Similarly, the layer next to the cathode needs to have the functionality of transporting electrons. In many instances, the hole-(electron) transporting layer also acts as the emitting layer. In some instances one layer can perform the combined functions of hole and electron transport and light emission. The individual layers of the organic film may be all polymeric in nature or combinations of films of polymers and films of small molecules deposited by thermal evaporation. It is preferred that the total thickness of the organic film be less than 1000 nanometers (nm). It is more preferred that the total thickness be less than 500 nm. It is most preferred that the total thickness be less than 300 nm. One embodiment of the instant invention is EL devices whose organic film comprises at least one of the polymeric compositions of this invention.

The ITO-glass which serves as the substrate and the anode may be used for coating after the usual cleaning with detergent, organic solvents and UV-ozone treatment. It may also be first coated with a thin layer of a conducting substance to facilitate hole injection. Such substances include copper phthalocyanine, polyaniline and poly(3,4-ethylenedioxy-thiophene) (PEDT); the last two in their conductive forms by doping with a strong organic acid, e.g., poly(styrenesulfonic acid). It is preferred that the thickness of this layer be 200 nm or less; it is more preferred that the thickness be 100 nm or less.

In the cases where a hole-transporting layer is used, the polymeric arylamines described in U.S. patent application Ser. No. 08/606,180, filed on Feb. 23, 1996; U.S. patent application Ser. No. 08/696,280, filed on Aug. 13, 1996; and U.S. patent application Ser. No. 08/696,281, filed on Aug. 13, 1996, may be used, all of which are hereby incorporated by reference. Other known hole-conducting polymers, such as polyvinylcarbazole, may also be used. The resistance of this layer to erosion by the solution of the copolymer film which is to be applied next is obviously critical to the successful fabrication of multi-layer devices. As the copolymers of this invention are applied as xylene or toluene solutions, the hole-transporting layer needs to be insoluble in these solvents. The thickness of this layer may be 500 nm or less, preferably 300 nm or less, most preferably 150 nm or less.

In the case where an electron-transporting layer is used, it may be applied either by thermal evaporation of low molecular weight materials or by solution coating of a polymer with a solvent that would not cause significant damage to the underlying film.

Examples of low molecular weight materials include the metal complexes of 8-hydroxyquinoline (as described by Burrows et al. in *Applied Physics Letters*, Vol. 64, pp. 2718–2720 (1994)), metallic complexes of 10-hydroxybenzo(h)quinoline (as described by Hamada et al. in *Chemistry Letters*, pp. 906–906 (1993)), 1,3,4-oxadiazoles (as described by Hamada et al. in *Optoelectronics—Devices and Technologies*, Vol. 7, pp. 83–93 (1992)), 1,3,4-triazoles (as described by Kido et al. in *Chemistry Letters*, pp. 47–48 (1996)), and dicarboximides of perylene (as described by Yoshida et al. in *Applied Physics Letters, Vol.* 69, pp. 734–736 (1996)).

Polymeric electron-transporting materials are exemplified by 1,3,4-oxadiazole-containing polymers (as described by Li et al. in *Journal of Chemical Society,* pp. 2211–2212 (1995), by Yang and Pei in *Journal of Applied Physics*, Vol 77, pp. 4807–4809 (1995)), 1,3,4-triazole-containing polymers (as described by Strukelj et al. in *Science* Vol. 267, pp. 1969–1972 (1995)), quinoxaline-containing polymers (as described by Yamamoto et al. in *Japan Journal of Applied Physics*, Vol. 33, pp. L250–L253 (1994), O'Brien et al. in Synthetic Metals, Vol. 76, pp. 105–108 (1996)), and cyano-PPV (as described by Weaver et al. in Thin Solid Films, Vol. 273, pp. 39–47 (1996)). The thickness of this layer may be 500 nm or less, preferably 300 nm or less, most preferably 150 nm or less.

The metallic cathode may be deposited either by thermal evaporation or by sputtering. The thickness of the cathode may be from 100 nm to 10,000 nm. The preferred metals are calcium, magnesium, indium, and aluminum. Alloys of these metals may also be used. Alloys of aluminum containing 1 to 5 percent of lithium and alloys of magnesium containing at least 80 percent of magnesium are preferred.

The EL devices of this invention emit light when subjected to an applied voltage of 50 volt or less with luminance efficiency as high as 3.5 Cd/A.

In a preferred embodiment, the electroluminescent device comprises at least one hole-transporting polymer film and a light-emitting polymer film comprised of the polymer of the invention, arranged between an anode material and a cathode material such that under an applied voltage, holes are injected from the anode material into the hole-transporting polymer film and electrons are injected from the cathode material into the light-emitting polymer films when the device is forward biased, resulting in light emission from the light-emitting layer. In another preferred embodiment, layers of hole-transporting polymers are arranged so that the layer closest to the anode has the lower oxidation potential, with the adjacent layers having progressively higher oxidation potentials. By these methods, electroluminescent devices having relatively high light output per unit voltage may be prepared.

The term "hole-transporting polymer film" as used herein refers to a layer of a film of a polymer which when disposed between two electrodes to which a field is applied and holes are injected from the anode, permits adequate transport of holes into the emitting polymer. Hole-transporting polymers typically are comprised of triarylamine moieties. The term "light-emitting polymer film" as used herein refers to a layer of a film of a polymer whose excited states can relax to the ground state by emitting photons, preferably corresponding to wavelengths in the visible range. The term "anode material" as used herein refers to a semi-transparent, or transparent, conducting film with a work function between 4.5 electron volts (eV) and 5.5 eV. Examples are oxides and mixed oxides of indium and tin, and gold. The term "cathode material" as used herein refers to a conducting film with a work function between 2.5 eV and 4.5 eV. Examples are lithium, calcium, magnesium, indium, silver, aluminum, or blends and alloys of the above.

Illustrative Embodiments

The following examples are included for illustrative purposes only and do not limit the scope of the claims. Unless otherwise stated, all parts and percentages are by weight.

EXAMPLE 1

2,7'-Dichloro-9,9-di(2-ethylhexyl)fluorene

To a stirred mixture of 2,7-dichlorofluorene (43 g, 0.183 mole) and 120 mL of dimethylsulfoxide (DMSO) under nitrogen is added benzyltriethylammonium chloride (2.3 g, 0.01 mole) and 60 mL of a 50 weight percent aqueous solution of sodium hydroxide. 2-Ethylhexyl bromide (85 g, 0.44 mole) is added and the mixture is agitated well for 2 hours. The reaction is exothermic, the temperature reaching 80° C. within 5 minutes after the addition of 2-ethylhexyl bromide and then falling off to 30° C. over the 2-hour reaction time. Analysis of an aliquot by high pressure liquid chromatography (HPLC) shows the complete disappearance of 2,7-dichlorofluorene and the formation of new product. Water (200 mL), and diethyl ether (250 mL) are added to the reaction mixture, stirred for 15 minutes and the layers are separated. The organic layer is washed with a saturated aqueous NaCl solution, water, dried ($MgSO_4$) and evaporated to remove ether. Fractional vacuum distillation of the residue provides 2,7-dichloro-9,9-di(2-ethylhexyl)-fluorene as clear liquid, boiling point 200° C./1 mm Hg, (79 g, 94 percent yield); HPLC analysis shows that the product is 99 percent pure. Proton Magnetic Spectrum (PMR) analysis is consistent with the title structure.

EXAMPLE 2

9,9-Di-n-butyl-2,7-dibromofluorene 2,7-Dibromofluorene (32.4 g, 0.1 mole), n-butyl bromide (75 g, 0.55 mole), tetra-n-butylammonium chloride (1.5 g) and 50 percent aqueous NaOH solution are stirred vigorously at 80° C. for 1 hour. The reaction mixture is allowed to cool to room temperature and extracted with ether. The ether extracts are washed with water and dried over anhydrous magnesium sulfate. Removal of solvent gives a yellow solid which is recrystallized from 400 mL of ethanol to provide 9,9-di-n-butyl-2,7-dibromofluorene as colorless crystals (42 g, 96 percent yield), melting point 120.5° C. to 121.5° C. HPLC analysis shows that the product has a purity of 99.5 percent and the proton and carbon-13 NMR are consistent with the title structure.

EXAMPLE 3

2,7-Dibromo-9,9-((2-methoxycarbonyl)ethyl) fluorene

To a 500 mL, three-necked, round-bottomed flask equipped with a condenser, magnetic stirring bar, stopper and a rubber septum is added 2,7-dibromofluorene (70.0 g, 0.216 mole) and methyl acrylate (166.0 g, 1.9 moles). To that stirring mixture is added dropwise (via syringe) benzyltrimethylammonium methoxide (3.3 mL, 40 weight percent solution). An exotherm is noted after addition of a few drops; temperature rose to 60° C. After the addition is completed, the reaction is stirred for an additional 15 minutes.

Excess methyl acrylate is distilled off under reduced pressure. The crude product solidifies after cooling to room temperature and is washed with hexane, then filtered. The crude solid is recrystallized from methanol to afford white crystals (79.0 g, 90 percent yield).

EXAMPLE 4

2,7-Dibromo-9,9-di(2-ethylhexyl)fluorene 2,7-Dibromo-9,9-di(2-ethylhexyl)fluorene, prepared from 2,7-dibromofluorene and 2-ethylhexyl bromide by the procedure of Example 1, is obtained as a pale-yellow syrup in 93 percent yield after passing the crude product through a column of silica gel and eluting the product with hexane. The carbon and proton magnetic spectra are found to be consistent with the title structure.

EXAMPLE 5

2,7-Dichloro-9,9-di(3-methyl-1-butyl)fluorene

Following the procedure of Example 1, 2,7-dichloro-9,9-di(3-methyl-1-butyl)fluorene is prepared from 2,7- dichlorofluorene and 1-bromo-3-methylbutane as colorless crystals (recrystallized from pentane) in 90 percent yield, melting point 116° C. to 117.5° C. The spectral data is consistent with the title structure and HPLC analysis shows the purity as 99 percent and greater.

EXAMPLE 6

2,7-Dichloro-9,9-di(1-hexyl)fluorene 2,7-Dichloro-9,9-di(1-hexyl)fluorene is prepared from 2,7-dichlorofluorene and 1-bromohexane following the procedure of Example 1 as colorless crystals (recrystallized from hexane) in 91 percent yield, melting point 66° C. to 67° C. HPLC analysis shows that the sample is 99 percent or greater pure and the spectral data confirms the title structure.

EXAMPLE 7

2,7-Dichloro-9-benzylidenylfluorene

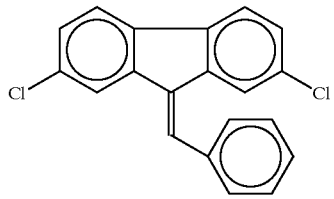

To a stirred suspension of 2,7-dichlorofluorene (6.4 g, 27 mmoles) in 30 mL of pyrrolidine or pyridine at 0° C. under nitrogen is added 6 mL of a 1M solution of tetrabutylammonium hydroxide in methanol. A solution of benzaldehyde (3.4 g, 32 mmoles) in 25 mL of pyridine is then added over 10 minutes and the orange-colored mixture is allowed to stir at ambient temperature for 2 hours. The mixture is poured into 300 mL of ice water, stirred for 3 hours, the yellow solid is filtered and recrystallized from n-heptane to provide 2,7-dichloro-9-benzylidenylfluorene as yellow needles, melting point 87° C. to 88° C. (7.8 g, 89.6 percent). PMR analysis is consistent with the title structure.

EXAMPLE 8

2,7-Dibromo-9-(4-dimethylamino-benzylidenyl) fluorene

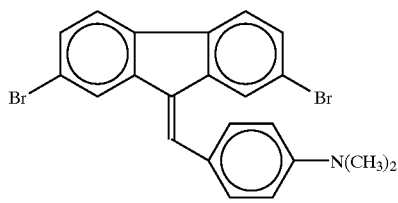

2,7-Dibromo-9-(4-dimethylamino-benzylidenyl)fluorene is prepared using the procedure of Example 1 in 87.7 percent yield as light-orange powder, melting point 214° C. to 216° C. (recrystallized from toluene). PMR analysis is consistent with the title structure.

EXAMPLE 9

2,7-Dibromo-9-(4-(2-ethylhexyloxy)benzylidenyl) fluorene

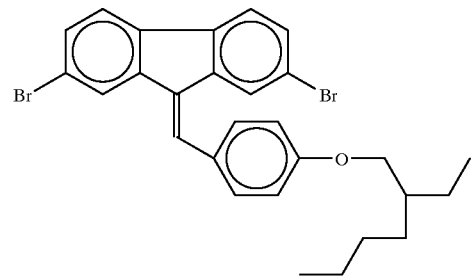

2,7-Dibromo-9-(4-(2-ethylhexyloxy)benzylidenyl) fluorene is prepared from 2,7-dibromo-9-fluorenene and 4-(2-ethylhexyloxyl)benzaldehyde using the procedure of Example 1 to give a yellow solid in 77 percent yield, melting point 68° C. to 70° C. PMR analysis is consistent with the title structure.

EXAMPLE 10

2,7-Dibromo-9-(3,5,5-trimethylhexylidenyl)fluorene

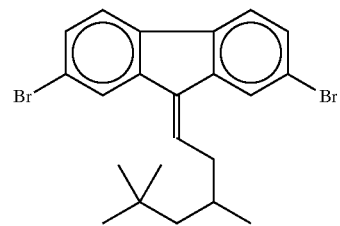

To a stirred mixture of 2,7-dibromofluorene (14 g, 40 mmoles) and pyridine (40 mL) under nitrogen at −15° C. is added 8 mL of a 1M solution of tetrabutylammonium hydroxide in methanol. A solution of 3,5,5-trimethylhexanal (7.6 g, 53 mmoles) in pyridine is added dropwise and the reaction mixture is stirred at ambient temperature overnight. The mixture is poured into 600 mL of ice water, stirred for 1 hour, the pale-yellow solid is isolated and recrystallized from ethanol to provide the title compound as pale-yellow powder, melting point 108° C. to 110° C. (11.6 g, 64.7 percent). PMR analysis is consistent with the assigned structure.

EXAMPLE 11

2,7-Dibromo-9-(5-norborn-2-enylidenyl)fluorene

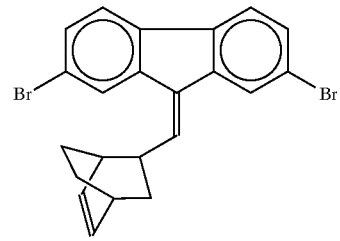

The title compound is prepared from 2,7-dibromofluorene and 5-norbornene-2-carboxaldehyde by following the procedure of Example 10. The product is extracted with ether and removal of ether gives a tan solid which is recrystallized from n-hexane to provide the title compound as tan crystals, melting point 118° C. to 120° C. (62 percent yield).

PMR analysis and HPLC shows the title compound is obtained as a 1:1 mixture of exo and endo isomers.

EXAMPLE 12

Poly(9,9-di-n-hexylfluorenyl-2,7'-diyl)

A dried polymerization reactor is charged with 2,7-dichloro-9,9-di-n-hexylfluorene (4.03 g, 10.0 mmoles), nickel chloride-2,2'-bipyridine complex (Ni complex) (43 mg, 0.15 mmole), zinc dust (1.96 g, 30 mmoles) and triphenylphosphine (TPP) (1.31 g, 5 mmoles). The reactor is evacuated and filled with nitrogen several times, and finally filled with argon. Dry dimethylacetamide (DMAc) (10 mL) is added and the contents of the reactor are stirred and heated in an 80° C. oil bath. After 4 hours, a solid polymer cake is formed and the oil bath temperature is raised to 90° C. After 5.75 hours, 10 mL of dry toluene is added and stirring and heating are continued. Two more 10 mL-portions of toluene are added at 6.5 hours and 7.3 hours. Heating and stirring are continued for 3.5 hours after the addition of the last portion of toluene. The mixture is poured into 150 mL of chloroform and filtered. The chloroform in the filtrate is removed on a rotary evaporator and the residue stirred with acetone. The large, bright-yellow granules obtained are dried for 18 hours in a vacuum oven at 70° C. The yield is 3.10 g, 93.9 percent. The polymer has the following structure:

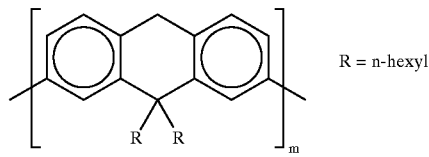

R = n-hexyl

The inherent viscosity is 0.57 dL/g. Gel permeation chromatography shows Mw 39,630 Daltons, Mn 16,020 Daltons and polydispersity of 2.47. The degree of polymerization, m, is 48. Differential scanning calorimetry (DSC) analysis at 5° C./minute shows two endothermic transitions centered at 193° C. and 249° C., indicative of liquid crystallinity. There is no indication of glass transition.

For comparison, Fukuda's polymer of formally the same chemical composition has a polydispersity of 6.8, degree of polymerization relative to polystyrene of 14, glass transition temperature of 55° C. and no crystallinity.

EXAMPLE 13

Poly(9,9-di-n-hexylfluorene-2,7'-diyl)

The experiment of Example 12 is repeated except the solvent is N-cyclohexylpyrrolidinone (20 mL). The polymerization is allowed to proceed for 18 hours and the product is purified and isolated as described in Example 12. The yield is 3.30 g, 100 percent. Inherent viscosity is 0.54 dL/g.

EXAMPLE 14

Poly(9,9-di-n-hexylfluorene-2,7'-diyl)

A dried polymerization reactor is charged with nickel chloride (52 mg, 0.4 mmole), 2,2'-bipyridine (62.4 mg, 0.4 mmole), zinc dust (5.76 g, 88 mmoles), and TPP (3.76 g, 14.0 mmoles). The reactor is evacuated and filled with nitrogen several times, and finally filled with argon. Dry DMAc (5 mL) is added and the content of the reactor stirred and heated in a 90° C. oil bath for 15 minutes to generate the active Ni(0) catalyst. A degassed solution of 2,7-dichloro-9,9-di-n-hexylfluorene (8.06 g, 20.0 mmoles) in 17 mL of dry DMAc is then added in two portions via a syringe and the polymerization is allowed to proceed for 4.5 hours. The polymer isolated has inherent viscosity of 0.35 dL/g.

A thin film of the polymer is melted on a glass slide and examined on a hot-stage microscope under cross-polarized light. Intense birefringence is observed at above 200° C., indicating that the polymer undergoes a crystalline to liquid crystalline transition as suggested by DSC analysis.

EXAMPLE 15

Photoluminescence of Poly(9,9-di-n-hexylfluorene-2,7'-diyl)

A dilute chloroform solution of the polymer prepared in Example 14 is spin-coated onto a quartz plate to give a dense, uniform film. Photoluminescence spectrum is obtained by excitation at 381 nm. The light emitted is intensely blue: major maximum at 424 nm with minor maxima at 445 and 475 nm. The emission spectrum reported by Fukuda consists of a broad peak centered at 495 nm and a very minor peak at 425 nm. The differences in the emission spectra are consistent with the fact that Fukuda's polymer is substantially different from the polymer of this invention.

EXAMPLE 16

Poly(9,9-di-(4-t-butyldimethylsilyloxy-phenyl)fluorene-2,7'-diyl)

To a reactor is added nickel chloride (27 mg, 0.2 mmole), 2,2'-bipyridine (34 mg, 0.22 mmole), zinc dust (1.5 g, 23 mmoles) and TPP (2.62 g, 10 mmoles). The reactor is evacuated and filled with argon several times. Dry DMAc (30 mL) is added and the contents stirred and heated in a 70° C. oil bath for 1 hour to generate the active catalyst. 2,7-Dibromo-9,9-di-(4-t-butyldimethylsilyloxyphenyl)fluorene (7.36 g, 10.0 mmoles) is added and the polymerization allowed to proceed for 23 hours. The solid mass is slurried with tetrahydrofuran (THF) and the slurry filtered to remove inorganic substances. The THF solution is stripped on a rotary evaporator and the residue extracted with ether. The ether-insoluble polymer is obtained as a yellow, granular solid and has an inherent viscosity of 0.28 dL/g. Gel permeation chromatography analysis shows Mw 31,120 Daltons and Mn 20,970 Daltons and polydispersity of 1.48. The polymer has the following structure:

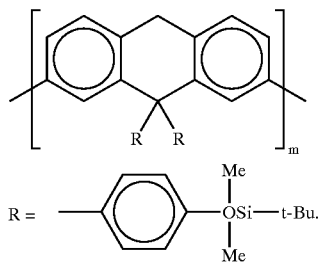

EXAMPLE 17

Poly(9,9-di-(4-(2-ethylhexanoyloxy)phenyl)fluorene-2,7'-diyl)

A reactor is charged with TPP (2.62 g, 10 mmoles), 2,7-dibromo-9,9-di-(4-(2-ethylhexanoyloxy)phenyl)

fluorene (8.9 g, 11.7 mmoles), potassium iodide (0.22 g, 1.3 mmoles), DMAc (29 mL) and toluene (10 mL). Traces of moisture are removed as an azeotrope with toluene. The reactor is heated in an oil bath at 70° C. and stirred under argon, and to it nickel chloride (26 mg, 0.2 mmole) and zinc dust (2.0 g, 30 mmoles) are added. After 20 hours, an additional portion of nickel chloride (20 mg) is added and the mixture allowed to react for another 24 hours. The solution is filtered to remove inorganic materials and the filtrate mixed with 300 mL of ether. The product is collected as bright-yellow granules by filtration and washed with more ether and dried in a vacuum oven at 70° C. overnight. The polymer has an inherent viscosity of 0.37 dL/g, Mw 36,280 Daltons, Mn 20,700 Daltons, polydispersity of 1.75. The structure of the polymer is as follows:

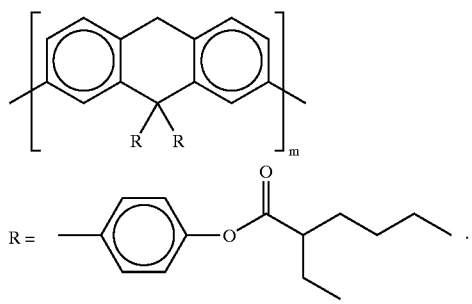

A solution of the resulting polymer in THF shows a broad absorption maximum at 389 nm, molar extinction coefficient of 50,000 and photoluminescent peaks at 417, 439, and 473 nm in decreasing intensity.

EXAMPLE 18

Poly(9,9-di(2-ethylhexyl)fluorene-2,7'-diyl)

A reactor is charged with 2,7-dibromo-9,9-di(2-ethylhexyl)fluorene (2.75 g, 5 mmoles), zinc dust (0.98 g, 15 mmoles), a NiCl$_2$-bipyridine complex (21.5 mg, 0.075 mmole), and TPP (0.66 g, 2.5 mmoles). The reactor is evacuated and filled with nitrogen several times. N-cyclohexylpyrrolidinone (3 mL) is added and the contents are stirred under nitrogen in a 80° C. oil bath. After 22 hours, the oil bath temperature is raised to 90° C. and the polymerization is allowed to proceed for a total of 31 hours. The reaction mixture is mixed with chloroform and filtered. The filtrate is concentrated and blended with methanol to give a yellow solid. The solid is dissolved in toluene (15 mL) and percolated through a short silica gel column with cyclohexane. The cyclohexane solution is concentrated and blended with methanol to precipitate the polymer as a yellow solid. Inherent viscosity is 0.15 dL/g. The structure of the polymer is as follows:

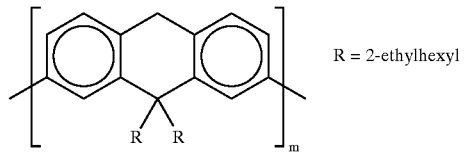

A small piece of the polymer is melted on a microscope slide at 230° C. and slowly cooled to room temperature while being examined under cross-polarized light. Birefringence emerged at 175° C. Heating the same film from room temperature reveals a liquid crystal to isotropic transition at 165° C.

EXAMPLE 19

Copolymer

To a reactor is added 2,7-dichloro-9,9-di(2-ethylhexyl) fluorene (0.92 g, 2 mmoles), 2,7-dichloro-9,9-di-n-hexylfluorene (3.2 g, 8 mmoles), TPP (1.31 g, 5.0 mmoles), NiCl$_2$-bipyridine complex (43 mg, 0.15 mmole) and zinc dust (1.96 g, 30 mmoles). The reactor is evacuated and filled with nitrogen several times and then to it is added DMAc (10 mL). The mixture is stirred at 80° C. for 7 hours and at 90° C. for 15 hours. The reaction mixture is mixed with chloroform and filtered. The filtrate is concentrated and the copolymer precipitates in acetone and dried in a vacuum oven at 50° C. overnight. The structure of the copolymer is as follows:

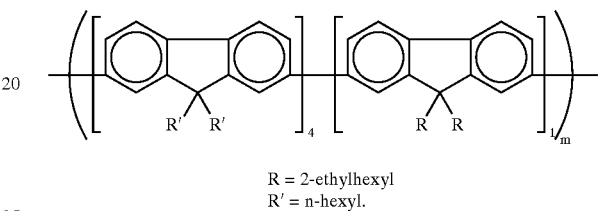

The copolymer has an inherent viscosity of 0.35 dL/g and a Tg at 89° C. as measured by DSC.

EXAMPLE 20

Poly(9,9-di(2-methoxycarbonylethyl)fluorene-2,7'-diyl)

A reactor is charged with TPP (2.0 g, 7.67 mmoles), zinc dust (2.02 g, 30.9 mmoles) and nickel bromide (0.22 g, 1.0 mmole). The reactor is evacuated and filled with nitrogen several times. To the reactor is added dimethylformamide (DMF) (5 mL) and the mixture is stirred at 40° C. for 15 minutes. Then, a solution of 2,7-dibromo-9,9-di(2-methoxycarbonylethyl)fluorene (4.96 g, 10 mmoles) in DMF (10 mL), previously flushed with nitrogen, is added. The polymerization is allowed to proceed for 48 hours at 80° C. The reaction mixture is dissolved in chloroform and filtered. The chloroform layer is washed with water and dried over anhydrous magnesium sulfate. Upon removal of the solvent, a yellow granular solid is obtained with the following structure:

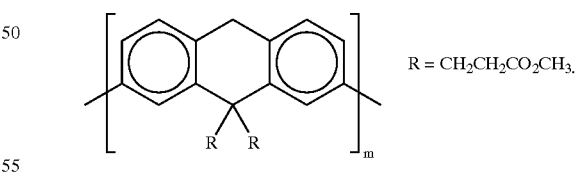

EXAMPLE 21

Benzocyclobutene (BCB)-capped oligo(9,9-di(2-ethylhexyl)fluorene-2,7'-diyl

A reactor is charged with 2,7-dibromo-9,9-di(2-ethylhexyl)fluorene (11.0 g, 20 mmoles), zinc dust (3.92 g, 60.0 mmoles), nickel complex (172 mg, 0.6 mmole) and TPP (2.62 g, 10 mmoles). The reactor is evacuated and filled with nitrogen several times. A solution of 4-bromobenzocyclobutene (Br-BCB) (1.10 g, 6 mmoles) in DMF (20 mL), previously flushed with nitrogen, is added to the reactor. The content is stirred at 75° C. under nitrogen for 24 hours. The reaction mixture is dissolved in 50 mL of toluene and filtered and the filtrate washed with water. The toluene solution is stirred at room temperature with 5 mL of 70 percent t-butylhydroperoxide overnight. Excess peroxide is decomposed with aqueous sodium hydrogen sulfite and the toluene solution washed with water and evaporated to dryness. The residue is extracted with hexane separating the desired product from triphenylphosphine oxide. The hexane solution is percolated through a silica gel column and evaporated to give 5.1 g of the following resin:

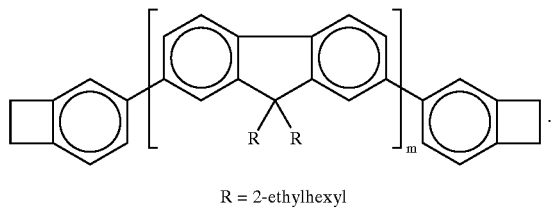

R = 2-ethylhexyl

Proton NMR analysis of the product indicates m=7.4.

A thin film of the material is examined on a hot-stage microscope under cross-polarized light. It is intensely birefringent, indicating presence of liquid crystallinity. Heating to 150° C. brings the disappearance of birefringence, which re-emerges upon cooling to room temperature.

EXAMPLE 22

BCB-capped oligo(9,9-di(2-ethylhexyl)fluorene-2,7'-diyl)

The experiment described in Example 21 is repeated with 5.55 g (10.0 mmoles) of fluorene monomer, 0.54 g (3 mmoles) of Br-BCB, 1.91 g (29.2 mmoles) of zinc dust, 79 mg (0.28 mmole) of nickel complex, 1.31 g (5 mmoles) of TPP and 10 mL of DMAc. The reaction is run at 80° C. for 16.5 hours. The product has the same structure as in Example 21 except m=7.2, as determined by proton NMR. A thin film of the resin is examined on a hot-stage microscope under cross-polarized light. The film is birefringent at room temperature, indicative of liquid crystallinity. Heating the film at 220° C. for 30 minutes and 250° C. for 1.5 hours gives an insoluble film, indicating that the BCB groups have substantially reacted, giving a crosslinked polymer.

EXAMPLE 23

BCB-capped oligo(9,9-di(2-ethylhexyl)fluorene-2,7'-diyl)

A 250 mL, three-necked, round-bottomed flask is charged with nickel chloride (0.156 g, 12 mmoles), 2,2'-bipyridine (0.188 g, 12 mmoles), TPP (5.24 g, 20 mmoles) and zinc dust (7.84 g, 120 mmoles) under nitrogen. 40 mL of DMAc is added via a syringe. The gray-colored slurry is stirred and heated at 80° C. for 15 minutes when the catalyst mixture turns reddish in color. A mixture of 2,7-dibromo-9,9-di(2-ethylhexyl)fluorene (21.94 g, 40 mmoles), Br-BCB (2.93 g, 16 mmoles), and 30 mL of DMAc is added to the catalyst dropwise over 15 minutes and the reaction mixture is stirred at 80° C. overnight.

The reaction mixture is cooled to room temperature, diluted with 200 mL of hexane and filtered through a bed of filter aid deatomaceous earth, and the filtered aid is washed with hexane (3×40 mL). To the filtrate is added 10 mL of a 70 percent t-butylhydro-peroxide solution and the resulting mixture is stirred at room temperature overnight and filtered through a filter aid. The top hexane layer of the filtrate is recovered, washed with saturated NaCl solution, water and dried over $MgSO_4$. The hexane solution is concentrated to 50 mL, cooled at 0° C. for a few hours to precipitate excess triphenylphosphine oxide, and the filtrate is evaporated to provide a yellow, semi-solid (16 g, 93 percent yield). The material is found to have a structure similar to that of Example 21 but with m=5.3.

Other properties of the material in the solid state are as follows: liquid crystallinity up to 100° C.; strong UV absorption (1 max 365 nm); and photoluminescence at 419 nm with minor peaks at 447, 473, and 511 nm in decreasing intensity. A thin film is cured at 200° C. for 1 hour, 225° C. for 1 hour and 250° C. for 1 hour. The UV absorption of the film is essentially the same before and after cure but the major photoluminescent peak has shifted to 512 nm.

EXAMPLE 24

BCB-capped oligo(9,9-di-n-hexyl)fluorene-2,7°-diyl)

A reactor is charged with 2,7-dichloro-9,9-di-n-hexylfluorene (8.1 g, 20 mmoles), Br-BCB (1.1 g, 6 mmoles), nickel complex (172 mg, 0.6 mmoles), zinc dust (3.92 g, 60 mmoles), TPP (2.62 g, 20 mmoles) and 30 mL of a 1:4 mixture of xylene and DMF. The reaction is stirred under nitrogen at 80° C. After 1.5 hours, an additional 10 mL of solvent mix is added and stirring is continued for 20 hours. The product mixture is dissolved in chloroform (100 mL) and filtered. Chloroform is removed under vacuum and the residue stirred with acetone (600 mL). The acetone-insoluble solid is isolated by filtration and dried in vacuo at 60° C. overnight to give 3.89 g of bright-yellow granules which was identified by proton NMR as follows:

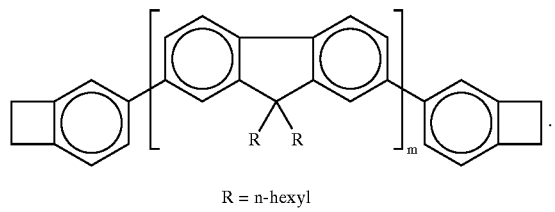

R = n-hexyl
m = 28.4

A solid film of this material shows UV absorption at 382 nm and photoluminescent peaks at 427, 440, and 481 nm in decreasing intensity.

The acetone solution is concentrated and mixed with ethanol (300 mL). The precipitated solid is isolated and dried to give 2.22 g of pale-yellow granules which is identified by proton NMR as follows:

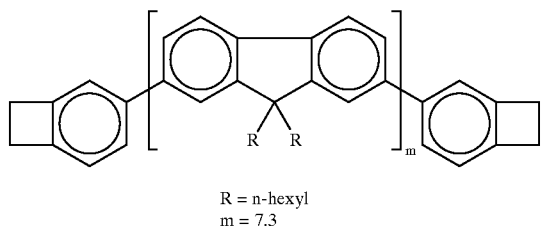

R = n-hexyl
m = 7.3

A solid film of this material shows UV absorption at 363 nm and photoluminescent peaks at 421, 442, and 475 nm in decreasing intensity.

Curing the above films as per the procedure of Example 22 does not bring significant shifts in the emission wavelengths. DSC analysis of both materials shows the expected exotherms due to crosslinking reactions of BCB.

EXAMPLE 25

BCB-capped oligo(9,9-di(2-methoxycarbonylethyl) fluorene-2,7'-diyl)

A reactor is charged with 2,7-dibromo-9,9-di(2-methoxycarbonylethyl)fluorene (9.92 g, 20 mmoles), nickel complex (172 mg, 0.6 mmole), zinc dust (2.93 g, 60 mmoles) and TPP (2.62 g, 10 mmoles). It is evacuated and filled with nitrogen several times. To it is added a solution of Br-BCB (1.46 g, 8 mmoles) in DMAc (30 mL), previously flushed with nitrogen for 45 minutes. The mixture is stirred at 80° C. for 20 hours. The reaction product is diluted with chloroform (300 mL) and filtered. The filtrate is concentrated and slurried with ethanol (300 mL) to give a fine, light-yellow solid which is filtered and washed with methanol. The product is dried in vacuum at 50° C. overnight. Proton NMR analysis indicates that the structure is as follows:

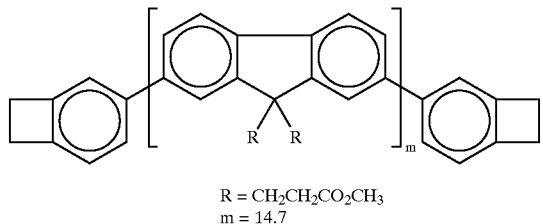

R = CH$_2$CH$_2$CO$_2$CH$_3$
m = 14.7

The resin shows multiple transitions during the first DSC scan from 25° C. to 300° C. A re-scan shows a Tg of 151° C. A solid film of this material shows UV absorption at 368 nm and photoluminescent peak at 431 and 466 nm of the same intensity, the latter being much broader. Curing the sample according to the procedure of Example 22 causes a shift of the emission peak to 540 nm.

EXAMPLE 26

BCB-capped oligo(9,9-di(2-ethylhexyl)fluorene-2,7'-diyl)

The experiment described in Example 21 is repeated with 37.9 g (60 mmoles) of 2,7-dibromo-9,9-di(2-ethylhexyl) fluorene, 11.8 g (180 mmoles) of zinc dust, 4.4 g (24 mmoles) of Br-BCB, 7.8 g (30 mmoles) of TPP, 0.52 g (1.8 mmoles) of nickel complex and 90 mL of DMAc. After 23 hours of reaction at 80° C., the content of the reactor is mixed with toluene and stirred with aqueous HCl to digest the excess zinc. The toluene solution is washed with water twice and evaporated to a yellow syrup which is dissolved in hexane (500 mL) and stirred overnight with 50 mL of 70 percent t-butylhydroperoxide. Excess peroxide is destroyed by stirring with an aqueous solution of sodium hydrogen sulfite and the hexane solution washed with water several times. The yellow oil obtained from evaporation of the solvent is passed through a short column (2-inch diameter and 2-inch height) of silica gel. The desired product is eluted with several liters of hexane. The combined hexane solution is again evaporated and the residue dissolved in 80 mL of toluene. The toluene solution is poured as a thin stream into 1.2 L of stirred methanol. The solid cake deposited is collected, dissolved in hexane and the solution dried over anhydrous magnesium sulfate. The solution is evaporated to leave an oil which is further stripped of volatile components at 90° C., 0.5 mm Hg, yielding 14.8 g of BCB-capped oligomer with the following structure:

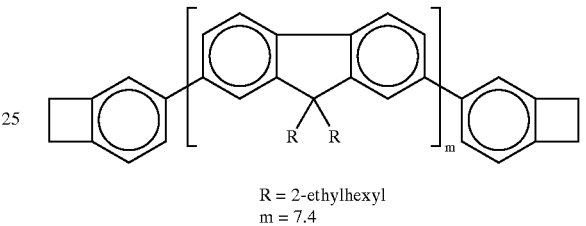

R = 2-ethylhexyl
m = 7.4

A one-gram sample of the material is placed in a round-bottom flask which is alternately evacuated and filled with argon several times. The flask is then placed in an oil bath heated to 150° C. and evacuated to 0.3 mm Hg for 30 minutes. After filling the flask with argon, the temperature of the bath is raised to 180° C. The sample is heated at this temperature for 24 hours and is allowed to cool under argon. DSC analysis shows that 44 percent of the BCB groups have reacted during the B-staging process. A xylene solution of the B-staged resin is used to spin-coat a quartz disk. The disk is heated in a nitrogen-purged oven from 25° C. to 250° C. at a ramp rate of 3° C./minute and holds at 250° C. for 1 hour. This provides a highly photoluminescent (blue), smooth, crosslinked film essentially free of pin-holes and other defects.

EXAMPLE 27

Hydroxyphenyl-capped oligo(9,9-di(2-ethylhexyl) fluorene-2,7'-diyl)

Example 21 is repeated with 19 g (30 mmoles) of 2,7-dibromo-9,9-di(2-ethylhexyl)fluorene, 6 g (90 mmoles) of zinc dust, 3.45 g (12 mmoles) of 4-bromophenyl-t-butyldimethylsilyl ether, 3.9 g (15 mmoles) of TPP, 0.26 g (0.9 mmole) of nickel complex and 50 mL of DMAc. The reaction is allowed to proceed at 80° C. for 21 hours. The reaction mixture is diluted with toluene (200 mL) and filtered through a filter aid to remove unreacted zinc. The filtrate is removed of toluene on a rotary evaporator and the residue shaken with water and extracted with hexane. The hexane solution is filtered through a filter aid again and the filtrate stirred with 15 mL of 70 percent t-butylhydroperoxide overnight. Excess peroxide is decomposed with aqueous sodium hydrogen sulfite and the solution washed repeatedly with water. Triphenylphosphine oxide is removed by filtration and the hexane solution is dried over anhydrous magnesium sulfate. Evaporation of hexane and further stripping of volatiles at 0.5 mm Hg, 120° C., 1 hour, gives a semi-solid. This is dissolved in toluene (60 mL) and the toluene solution pours as a thin stream into methanol. The semi-solid precipitated cake is dissolved in hexane. The hexane solution yields 10.0 g of strongly photoluminescent (blue) semi-solid after drying and stripping. The NMR spectrum of this material is consistent with the expected structure as follows:

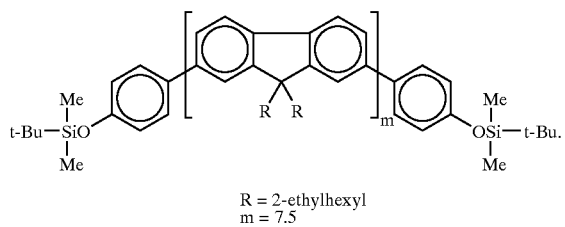

R = 2-ethylhexyl
m = 7.5

The above material is refluxed with a solution of tetrahydrofuran (100 mL) and concentrated HCl (5 mL) for 6 hours to effect desilylation. The NMR spectrum of the product is consistent with the expected structure as follows:

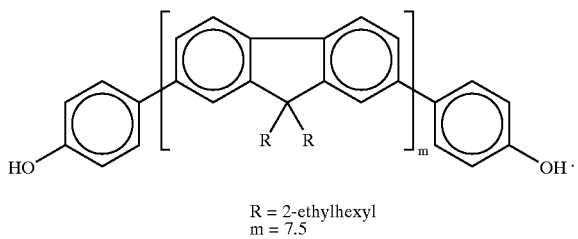

R = 2-ethylhexyl
m = 7.5

EXAMPLE 28

Cyanatophenyl-capped oligo(9,9-di(2-ethylhexyl) fluorene-2,7'-diyl)

The phenolic material from Example 27 (6.5 g) is dissolved in methylene chloride (75 mL) and mixed with 2.5 g of cyanogen bromide in a reactor. The resulting solution is cooled to −20° C. and to it is added a solution of 3 mL triethylamine and 10 mL methylene chloride over a period of 3 minutes. The mixture is stirred at −10° C. for 1 hour and is then washed with dilute HCl, water and dried over anhydrous magnesium sulfate. Removal of solvent gives 6.5 g of light-brown oil showing the expected infrared absorption bands (2200 to 2300 cm$^{-1}$) for cyanate groups and no absorption band for phenolic groups. The oil is further purified by passage through a short silica gel column to give a strongly photoluminescent (blue), yellow semi-solid. The NMR and infrared spectra of the material are consistent with the following structure:

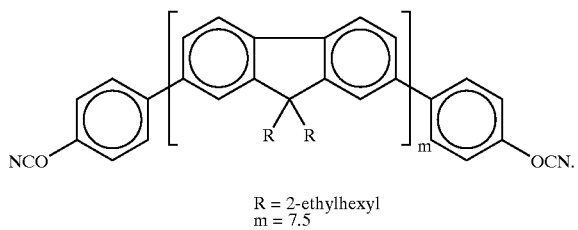

R = 2-ethylhexyl
m = 7.5

EXAMPLE 29

Polymerization of 2,7-dichloro-9-benzylidenylfluorene

To a dry reactor equipped with a mechanical stirrer, rubber septa, and an inlet connected to a vacuum and nitrogen manifold is added TPP (2.00 g, 8 mmoles), zinc dust (3.02 g, 31 mmoles), and nickel complex (0.26 g, 1 mmole). The reactor is evacuated and purged with nitrogen 7 times and is heated to 40° C. 1-Methyl-2-pyrrolidinone (NMP) (10 mL) is added via a syringe. The reaction mixture is stirred at approximately 250 rpm. After a few minutes, the solution turns to a reddish-brown color. To the reaction mixture is added a solution of 2,7-dichloro-9-benzylidenylfluorene (3.23 g, 10 mmoles) in NMP (7.0 mL). The reaction is stirred at 80° C. for 48 hours.

The reaction mixture is poured into acetone (300 mL) to precipitate the polymer. The orange-gray precipitate is collected and washed with acetone (2×100 mL). After drying in air, the solid is crushed to a powder and the powder is slowly added to 250 mL of 3N HCl. The mixture is stirred for 3 hours, at which point the precipitate is a bright-orange color. The solid is collected, washed with water (3×100 mL) then air-dried overnight. The solid is then dried in a vacuum oven at 60° C. overnight to afford 2.46 g (98 percent yield) of an orange powder. Based on the yield and spectral data, the structure of the polymer is as follows:

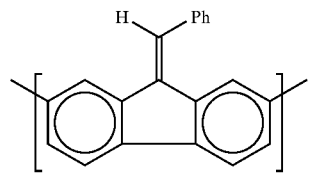

A film of the polymer, cast onto a quartz disk from a chloroform solution, shows a strong UV absorption band centered at 368 nm and a broad photoluminescent band centered at 571 nm.

EXAMPLE 30

Copolymerization (1:1) of 2,7-dichloro-9-benzylidenylfluorene and 2,7-dichloro-9,9-di-n-hexylfluorene The procedure of Example 29 is repeated with 1.62 g (5 mmoles) of 2,7-dichloro-9-benzylidenylfluorene and 2.02 g (5 mmoles) 2,7-dichloro-9,9-di-n-hexylfluorene in DMAc (15.0 mL). The reaction mixture is stirred at 80° C. for 48 hours. The reaction mixture is added to methylene chloride (200 mL) and the resulting solution is filtered through a plug of filter aid to remove the unreacted zinc. The filtered solution, after concentration, is slowly added to acetone (300 mL) to precipitate the product. The bright-yellow precipitate is collected and washed with acetone (3×50 mL) and dried to give 1.79 g of 1:1 copolymer whose structure could be alternating as shown below or could consist of blocks of the two monomeric units. A film, cast on a quartz disk from a chloroform solution, shows a strong UV absorption band centered at 370 nm and photoluminescent bands centered at 417 and 551 nm. This copolymer is represented by the following structure:

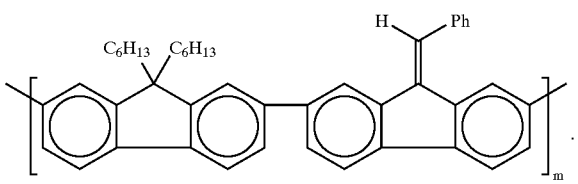

EXAMPLE 31

Copolymerization (1:4) of 2,7-dichloro-9-benzylidenylfluorene and 2,7'-dichloro-9,9-di-n-hexylfluorene Example 30 is repeated with 0.65 g (2 mmoles) of 2,7-dichloro-9-benzylidenyl-fluorene and 3.23 g (8 mmoles) of 2,7'-dichloro-9,9-di-n-hexylfluorene in NMP (15 mL). The reaction mixture is stirred at 80° C. for 48 hours and is then added to methylene chloride (200 mL). The methylene chloride solution is filtered through a plug of filter aid to remove the zinc. The filtered solution, after concentration, is slowly added to acetone (200 mL) to give 1.0 g of yellow polymer. The acetone solution is concentrated and slowly added to ethanol (200 mL) to precipitate an additional portion of polymeric product (1.3 g). Based on the yield and spectral data, the structure of the polymer is as follows:

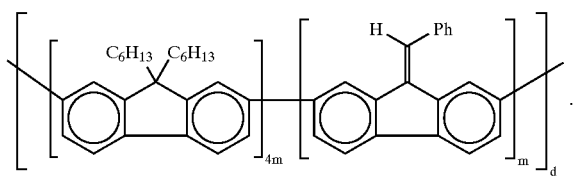

A film, cast on a quartz disk from a chloroform solution, shows a strong UV absorption band centered at 370 nm and photoluminescent bands centered at 470 and 522 nm.

EXAMPLE 32

Polymerization of 2,7-dichloro-9-(3,5,5-trimethylhexylidenyl)fluorene

The procedure of Example 29 is repeated with 4.5 g (10 mmoles) of 2,7-dichloro-9-(3,5,5-trimethylhexylidenyl) fluorene in DMF (15 mL). The reaction mixture is stirred at 80° C. for 28 hours. The reaction mixture is added to acetone (200 mL) to precipitate the product. The precipitate is collected, air-dried, crushed to a powder, then added to an aqueous solution of 3N HCl (300 mL). The mixture is stirred for 3 hours to dissolve the zinc metal. The bright, yellow-orange precipitate is collected, washed with methanol (3×100 mL) and acetone (3×100 mL) and then dried to give 2.5 g of product. The product is soluble in hot 1,2-dichlorobenzene. The melting point is 306° C.

EXAMPLE 33

Polymerization of 2,7-dichloro-9-(5-norbornenylid-2-ene)fluorene

The procedure of Example 29 is repeated with 4.3 g (10 mmoles) of 2,7-dichloro-9-(5-norbornenylid-2-ene)fluorene in DMF (20 mL). The reaction mixture is stirred at 80° C. for 26 hours. The reaction mixture is added to acetone (200 mL) to precipitate the product. The precipitate is collected, air dried, crushed to a powder, then added to an aqueous solution of 3N HCl (300 mL). The mixture is stirred for 3 hours to dissolve the zinc metal. The precipitate is collected, washed with methanol (3×100 mL) and acetone (3×100 mL) and then dried to give 3.0 g of product.

EXAMPLE 34

General Procedure for the Preparation of a 9,9-Disubstituted 2,7-Fluorene Diboronate (Compounds Shown in Table 1)

To a stirred mixture of a 9,9-disubstituted 2,7-dibromofluorene (10 mmoles) and 50 mL of tetrahydrofuran (THF) under nitrogen at −78° C. is added dropwise a 2.5 M solution of n-butyllithium in hexane (8 mL, 20 mmoles) over 10 minutes. The dilithio intermediate precipitates in a few minutes and the resulting colorless suspension is stirred at −78° C. for 1 hour. Tri-isopropylborate (7.5 g, 40 mmoles) is added all at once, and the resulting slurry (additional 20-30 mL of THF is added to facilitate agitation, in some cases) is stirred for 1 hour at −78° C., 16 hours at room temperature, and poured into 300 mL of ice water containing 25 mL of concentrated HCl. After stirring for 30 minutes, the product is extracted with 2×150 mL of diethyl ether. The ether extracts are washed with saturated aqueous sodium chloride solution (200 mL), dried ($MgSO_4$) and rotary evaporated to remove the solvent providing the diboronic acid as a semi-solid. The purity of the crude diboronic acid is assessed to be 85 to 95 percent depending upon the substrate by HPLC analysis and is converted to the diboronate without further purification, as described below.

The crude diboronic acid is suspended in 50 mL of toluene, 30 mmoles (1.86 g) of ethylene glycol is added, and the mixture is stirred and refluxed under a Dean-Stark trap for 2 to 3 hours. During this time, about 25 mL of toluene is collected as over-head along with a small amount of water formed during the reaction as an azeotrope. The reaction mixture is cooled and the solvent is removed. The residue (semi-solid) is recrystallized from hexane or toluene-hexane mixture, depending upon the substrate, to provide the diboronate as colorless, amorphous powder in 70–85 percent overall yield. The purity, as judged by HPLC, is about 95 to 99 percent. Further recrystallization provides material of 99+percent purity. Proton magnetic spectrum (PMR) in $CDCl_3$ reveals the presence of the methylene hydrogens of the boronate as a singlet at a chemical shift of 4.4 ppm relative to tetramethylsilane (internal standard). The diboronates of 9,9-disubstituted fluorenes used in this invention are given in Table 1.

Preparation of Dibromoarenes (Compounds Shown in Tables 2 and 3)

1,4-Dibromonaphthalene (M-16), 2,5-dibromothiophene (M-11), and 9,10-dibromoanthracene (M-18) are available commercially from Acros Organics, a division of Fisher Scientific Co. or Aldrich Chemicals. 5,5'-dibromo-2,2'-bithiophene (M-12) is prepared by bromination of 2,2'-bithiophene, as reported by R. M. Kellogg, A. P. Schaap, and H. Wynberg in *Journal of Organic Chemistry*, Vol. 34, pp. 343–346 (1969). 4,7-dibromo-2,1,3-benzothiadiazole (M-15) is prepared by bromination of 2,1,3-benzothiadiazole as reported by K. Pilgram, M. Zupan, and R. Skiles in *Journal of Heterocyclic Chemistry*, Vol. 7, pp. 629–633 (1970). 3,6-Dibromo-1,2-phenylenediamine is synthesized from 4,7-dibromo-2,1,3-benzothiadiazole as reported for the selenium analog reported by C. W. Bird, G. W. H. Cheeseman, and A. A. Sarsfield in *Journal of Chemical Society*, pp. 4767–4670 (1963) and was converted to 5,8-dibromo-2,3-diphenylquinoxaline (M-17) as reported in the same reference.

2,7-Dibromo-9,9-bis(4-phenoxyphenyl)fluorene (M-10)

To a stirred mixture of 2,7-dibromofluorenone (26 g, 77 mmoles) and phenyl ether (170 g, 1 mole) is added 60 mL of methanesulfonic acid and 0.5 mL of 3-mercaptopropionic acid. The mixture is heated and stirred at 60° C. for 30 minutes, and then at 25° C. for 16 hours. The mixture is again stirred at 60° C. for 30 minutes and then at 25° C. for 3 hours. The mixture is poured into 1.4 L of ice water and 200 mL of methanol and allowed to stand in the hood for 4 days. The semi-solid precipitate is separated by decanting the supernatant liquid and then digesting with 1:1 v/v acetonitrile-hexane. The title compound is obtained as a colorless powder (32 g, 64 percent), melting point 178° C. to 180° C. HPLC analysis shows a purity of greater than 99 percent and the PMR spectrum (DMSO-$d_6$) is consistent with the structure.

1,4-Dibromo-2,5-Dimethoxybenzene (M-14)

To a solution of 1,4-dimethoxybenzene (13.8 g, 0.1 mole) in 100 mL of carbon tetrachloride is added a solution bromine (32 g, 0.2 mole) in 50 mL of carbon tetrachloride dropwise. The resulting solution is stirred at room temperature for 2 days. Evaporation of the solvent and recrystallization of the residue from ethanol-toluene gave 24.5 g (82.8 percent yield) of the desired product. The $^1$H NMR spectrum is consistent with the structure of the desired product.

2,5-Bis(4'-bromostyryl)-1,4-dicyanobenzene (M-21)

A mixture of 1,4-dibromo-p-xylene (52.8 g, 0.2 mole), CuCN (53.4 g, 0.6 mole), and DMF (150 mL) is refluxed for about 19 hours. The yellow crystals formed are isolated by pouring the slurry into water and filtration. The crude product is stirred with a mixture of 500 mL of water and 100 mL of ethylenediamine until the yellow color has disappeared. The grey crystalline solid is added to a solution containing 200 mL of water, 50 mL of conc. HCl, and 50 g of ferric chloride hexahydrate and the resulting slurry stirred is warmed to about 50° C. for 30 minutes. The off-white crystalline solid is collected by filtration and recrystallized from 1.8 L of ethanol, yielding 24.0 g (77 percent yield) of 1,4-dicyano-p-xylene.

1,4-Dicyano-p-xylene (15.6 g, 0.1 mole), N-bromosuccinimide (40.0 g, 0.22 mole) and carbon tetrachloride (200 mL) are refluxed with stirring for 4 days. The succinimide formed is removed by filtration and the filtrate concentrated to a yellow oil which solidifies on standing. The crude product is repeatedly recrystallized from ethanol until it is about 90 percent 1,4-dicyano-2,5-bis(bromoethyl)benzene. About 5.7 g of the crude product is refluxed with 8.0 g of triphenylphosphine in 100 mL of toluene and 30 mL of DMF for about 22 hours. The thick paste is diluted with 200 mL of ether and the solid collected by filtration. After washing with more ether and drying, about 11 g of 2,5-dicyano-p-xylylenebis(triphenylphosphonium bromide) is obtained.

2,5-Dicyano-p-xylylenebis(triphenylphosphonium bromide) (recrystallized from methanol) (7.1 g, 8.6 mmoles) and 4-bromobenzaldehyde (3.3 g, 18 mmoles) are suspended in 60 mL of ethanol and a 1M solution of lithium ethoxide in ethanol (20 mL) is added dropwise over 20 minutes with good agitation. After stirring at 25° C. for 4 hours, the precipitate is filtered and recrystallized from DMF to provide the title compound as a pale-yellow solid (60 percent). HPLC analysis and PMR spectrum in DMSO-$d_6$ confirm that the material (M-21) is a mixture of cis and trans isomer in the ratio of 7:93.

α,α-Bis(4-bromophenylmethylene)-1,4-benzenediacetonitrile (M-22)

A mixture of 4-bromobenzaldehyde (24.0 g, 0.13 mole), phenylene-1,4-diacetonitrile (10.0 g, 0.064 mole), piperidine (5 mL), and ethanol (150 mL) is refluxed for 3 hour sand the mixture allowed to stand overnight at room temperature. The orange crystalline solid is filtered and washed three times with ethanol (200 mL) and dried to give 15.3 g (50 percent) of the desired product. The $^1$H NMR spectrum is consistent with the structure of the desired product. Recrystallization from DMF provides a very pure product for polymerization.

4-Methyl-4,4"-bis(2-β-bromophenyl-5-oxadiazolyl)-triphenylamine (M-24)

The bis-hydrazide (obtained from 4-methyl-4',4"-bis (benzoichydrazide)-triphenylamine and 2 equivalents of 4-bromobenzoyl chloride in pyridine at 100° C. for 90 minutes) (12 g) is mixed with 50 mL of chlorobenzene and 25 mL of trimethylsilylpoly-phosphate and the suspension is stirred and heated under nitrogen for 3 hours. The mixture is cooled, added to a mixture of 200 mL of water and 200 mL of ethanol, stirred for 1 hour and the pale-yellow solid is filtered. Recrystallization from DMF provides the title compound as pale-yellow crystals (8.5 g, 76 percent). The PMR spectrum in DMSO-$d_6$ is found to be consistent with the assigned structure.

1,4-Di(4-bromostyryl)benzene (M-20)

A 250 mL, three-necked, round-bottom flask, equipped with an overhead stirrer and an addition funnel which is connected to a nitrogen line, is charged with p-xylylenebis-(triphenylphosphonium bromide) (8.05 g, 10 mmoles), 4-bromobenz-aldehyde (3.75 g, 20 mmoles) and ethanol (100 mL). To the mixture with stirring is added dropwise a solution of lithium ethoxide (1.0 M in ethanol, 21.5 mL, 21.5 mmoles), and the resulting mixture is stirred at ambient temperature for 6 hours. (The mixture remains heterogeneous through out the reaction.) At the end of the reaction, the crude product is collected by filtration, and redissolved in toluene (100 mL). (A cloud solution was observed). The solution is washed with aqueous hydrochloric acid (5 percent, 50 mL), water (3×40 mL) and dried with magnesium sulfate. The solvent is evaporated under vacuum and the residue is crystallized with the addition of methanol. The product is collected by filtration, washed with methanol and dried in a vacuum oven at 60° C. overnight to afford 3.6 g (82 percent) as white needles.

2,3-Bis(4-bromophenyl)-2,3-butenedinitrile (M-19)

A solution of 4-bromobenzyl cyanide (43.5 g, 0.222 mole) in carbon tetrachloride (100 mL) is added slowly, over a period of 30 minutes, to a rapidly stirring mixture of 40 percent aqueous sodium hydroxide (100 mL) and benzyltriethyllammonium chloride (0.68 g, 0.003 mole). The mixture is stirred at ambient temperature overnight, after which time a reddish precipitate has formed which is collected by filtration. The reddish solid is digested with hydrochloric acid (5 percent/ethanol) to provide a cream-colored solid, which is collected by filtration, washed with methanol and dried in air. Recrystallization from methylene chloride/methanol affords 11 g of light-yellow solid.

Above organic mother liquors are combined, washed successively with diluted hydrochloric acid (5 percent), and aqueous sodium bicarbonate (5 percent) and water, and then dried over magnesium sulfate. The dried solution is filtered, and then evaporated to a paste which is titrated with ethanol to give a second crop of product (7 g). The total yield was 18 g (42 percent).

Preparation of N,N-di(4-bromophenyl)-p-tolylamine (M-23)

To a stirred solution of N,N-diphenyl-p-tolylamine (99.7 g, 0.38 mol) in DMF (300 mL) is slowly added a solution of N-bromosuccinimide (138.2 g, 0.78 mol) in 300 mL of DMF while maintaining a reaction temperature of about 40° C. After the addition, the solution is poured into cold water (500 mL), stirred for 1 hour, and the solids are filtered and recrystallized from ethanol to provide the title compound as colorless crystals (135.4 g, 85 percent). The proton and the carbon magnetic resonance spectra are in agreement with the assigned structure.

N,N'-Di(4-bromophenyl)-N,N'-di(ethyl 3-phenylcarboxylate)-benzidine (M-25)

N,N'-di(ethyl 3-phenylcarboxylate)-benzidine (6.3 g) is dissolved in DMF (70 mL). To the solution N-bromosuccinimide (3.6 g) is added in small potions with stirring. The resultant mixture is stirred at ambient temperature for 3 hours. To the mixture is then added ethanol (200 mL) and the stirring is continued for 1 hour. The crude product is collected by filtration, washed with ethanol and dried in air. The product is recrystallized from toluene-ethanol to give 6.4 g of white needles.

N,N'-Di-(4-bromophenyl)-N,N'-di-(ethyl 3-phenylcarboxylate)-1,4-phenylenediamine (M-26)

N,N'-Diphenyl-N,N'-di-(ethyl 3-phenylcarboxylate)-1,4-phenylenediamine (28.8. g) is dissolved in DMF (500 mL). To the solution N-bromosuccinimide (20.3 g) is added in small potions with stirring. The resultant mixture is stirred at ambient temperature for 3 hours. To the mixture is then added ethanol (600 mL) and the stirring is continued for 1 hour. The crude product is collected by filtration, washed with ethanol and dried in air.

The product is recrystallized from toluene-ethanol to give 31.4 g of white needles.

General Procedure for the Polymerization Reaction (Except Polymer 28)

To a stirred mixture of the 9,9-disubstituted 2,7-fluorene diboronate (6 mmoles), dibromoarene (6 mmoles), and toluene (45 mL) under nitrogen is added 1 g of the phase transfer catalyst (ALIQUAT 336®, available from Aldrich Chemicals), tetrakis(triphenylphosphine)palladium(0) (70 mg, 0.06 mmole), and 2M aqueous sodium carbonate solution (10 mL). The mixture is stirred and heated to gentle reflux in an oil bath under nitrogen for 20 hours. Bromobenzene (1 mL) is added and the reaction is refluxed for an additional hour. The reaction mixture is cooled, poured slowly into a mixture of methanol-water (1 L, 9:1 v/v) in a blender with good agitation. The precipitated polymer fibers are collected by filtration, washed with 200 mL of methanol, and dried. The crude yield is 95 to 99 percent. Further purification of the polymer is carried out as follows:

The polymer is dissolved in 200 mL of toluene (gentle warming was necessary in most cases to effect rapid dissolution), and the solution is washed successively with deionized water (DI water) (200 mL), 6N aq. HCl solution (2×120 mL), DI water (200 mL), 10 percent (v/v) aq. solution of ethylene diamine (2×100 mL), DI water (200 mL), 2N aq. HCl solution (150 mL), and finally with DI water (200 mL). The solution is then passed through a column (1 inch in diameter) packed with 2 inches of filtering aid and two inches of silica gel, eluted with 2×200 mL of toluene, and the combined eluates are concentrated to about 60 mL, and poured slowly into a stirred mixture of methanol-acetone (1.1 L, 8:3 v/v). The precipitated fibers are collected and subjected to another dissolution-reprecipitation procedure. The purified polymers are isolated in 70 to 90 percent yield after drying in a vacuum oven under nitrogen at 50° C. for 24 hours. Further characterizations of the polymers by differential scanning calorimetry (DSC), absorption and photoluminescence spectrometry (PL) and inherent viscosity are carried out and the data are given in Table 4. The copolymers typically have inherent viscosities (25° C., 0.5 g/dL) in the solvent shown in Table 4) of about 1.0 dL/g which corresponds to about 100,000 Daltons by gel permeation chromatography relative to polystyrene with polydispersity typically less than or equal to 3.0.

Preparation of Polymer 28 (P-28)

This example illustrates the preparation of a copolymer in which an oligomeric fluorene copolymer is uniformly incorporated into a homopolymer of 9,9-di-n-octylfluorene.

To a stirred solution of 9,9-di-n-octylsfluorene-2,7-bisboronate (M-27) (318 mg, 0.6 mmole) in toluene (18 mL) under a nitrogen atmosphere is added M-22 (245 mg, 0.5 mmole), tetrakis(triphenylphosphine)palladium (25 mg, 0.02 mmole), ALIQUAT 336® (200 mg), and 2 mL of 2M aq. sodium carbonate solution. The mixture is stirred and gently refluxed in an oil bath for 16 hours. The mixture is cooled to 50° C., and then the following ingredients are syringed in as a solution in 35 mL of toluene: diboronate M-27 (5.13 g, 9.4 mmoles), dibromofluorene (M-3) (5.21 g, 9.5 mmoles), the palladium catalyst (25 mg), 1 g of ALIQUAT 336®, and 10 mL of 2M sodium carbonate solution. The mixture is again heated and stirred under reflux for an additional 22 hours. The reaction mixture is cooled and worked up as reported in the general procedure to provide 6.75 g (87 percent yield) of the title polymer as bright yellow fibers. The inherent viscosity in THF at 25° C. is found to be 1.33 dL/g (0.5 g/100 mL).

Hydrolysis of Polymer 32 (P-32)

A 500-mL, round-bottom flask, equipped with a reflux condenser which was connected to a nitrogen line, is charged with 2 g of P-32, aqueous solution of potassium hydroxide (1 g in 20 mL of water) and THF (200 mL). The mixture is stirred and refluxed under nitrogen for 20 hours. At the end of the reaction a light-yellow polymer precipitate is observed. After cooling, a solution of diluted hydrochloric acid (2 mL concentrated acid in 5 mL of water) is added. The mixture is stirred for about 30 minutes until all the precipitate has dissolved. Most of the solvent is removed by rotary evaporation and the polymer is precipitated by adding the residual solution to acetone (300 mL). The polymer is collected by filtration, washed thoroughly with water and dried in air. The polymer is redissolved in THF (100 mL), and concentrated by rotary evaporation. The product is precipitated from methanol (400 mL), collected by filtration, washed with methanol and dried in a vacuum oven at 70° C. overnight to give 1.54 g (81.5 percent) of light-yellow fibrous polymer of the following structure:

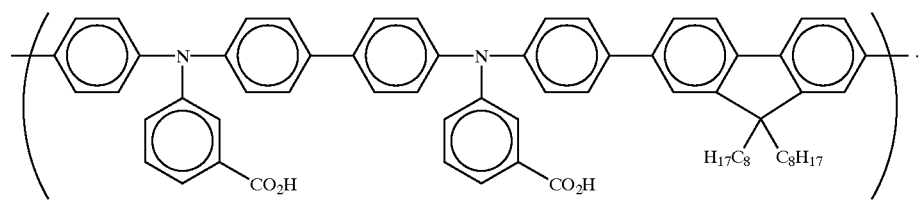

TABLE 1
2,7-Dibromofluorenes
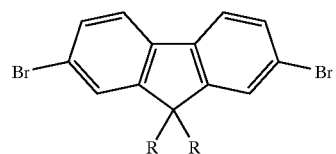
| | |
|---|---|
| M-1 | R = —CH$_2$(CH$_2$)$_4$CH$_3$ |
| M-2 | R = —CH$_2$CH(CH$_2$CH$_3$)CH$_2$(CH$_2$)$_2$CH$_3$ |
| M-3 | R = —CH$_2$(CH$_2$)$_6$CH$_3$ |
| M-4 | R = —CH$_2$CH$_2$CH(CH$_3$)CH$_2$(CH$_2$)$_2$CH$_2$CH(CH$_3$)CH$_3$ |
| M-5 | R = —CH$_2$(CH$_2$)$_9$CH$_3$ |
| M-6 | R = —CH$_2$(CH$_2$)$_{10}$CH$_3$ |
| M-7 | R = —CH$_2$CH$_2$OCH$_3$ |
| M-8 | R = —CH$_2$CH$_2$OCH$_2$CH$_2$OCH$_3$ |
TABLE 1-continued
2,7-Dibromofluorenes
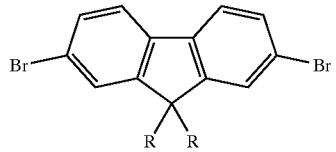
M-9   R = 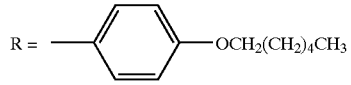
M-10  R = 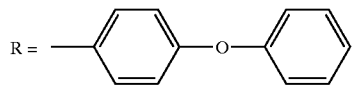
TABLE 2
Aromatic Dibromide Monomers
M-11 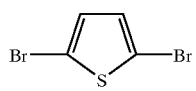
M-12 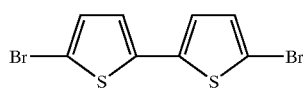
M-13 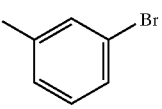
M-14 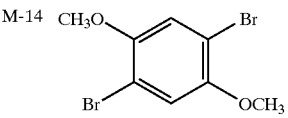
M-15 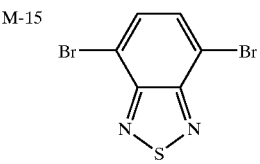
M-16 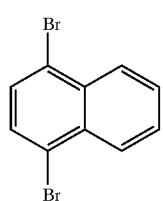

TABLE 2-continued
Aromatic Dibromide Monomers
M-17
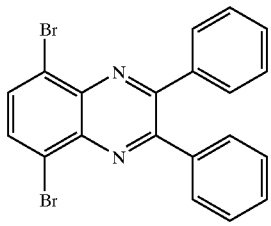
M-18
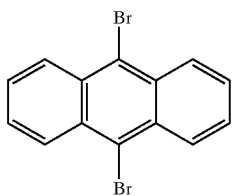
M-19
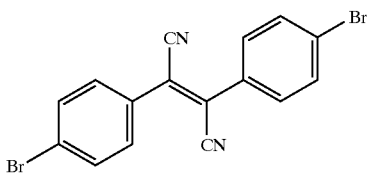
M-20
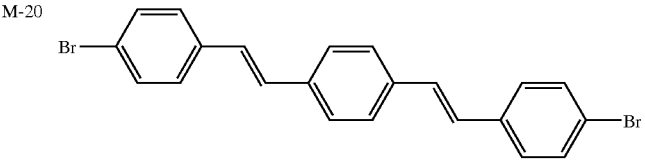
M-21
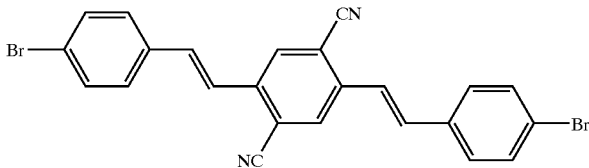
M-22
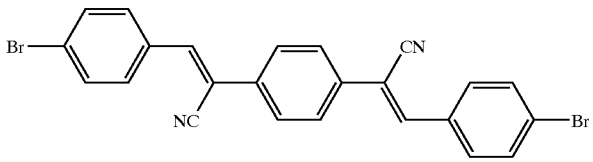
M-23
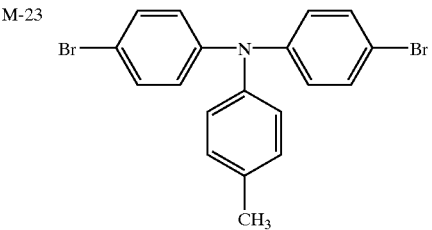

TABLE 2-continued

Aromatic Dibromide Monomers

M-24

M-25

M-26

M-27

TABLE 3

Fluorene Diboronic Ester Monomers

| | |
|---|---|
| M-28 | R = —CH$_2$(CH$_2$)$_4$CH$_3$ |
| M-29 | R = CH$_2$CH(CH$_2$CH$_3$)CH$_2$(CH$_2$)$_2$CH$_3$ |
| M-30 | R = —CH$_2$(CH$_2$)$_6$CH$_3$ |
| M-31 | R = CH$_2$(CH$_2$)$_9$CH$_3$ |
| M-32 | R = —CH$_2$(CH$_2$)$_{10}$CH$_3$ |
| M-33 | R = —CH$_2$CH$_2$OCH$_2$CH$_2$OCH$_3$ |
| M-34 | R = —CH$_2$CH$_2$CH(CH$_3$)CH$_2$(CH$_2$)$_2$CH$_2$CH(CH$_3$)CH$_3$ |

TABLE 3-continued

Fluorene Diboronic Ester Monomers

| | |
|---|---|
| M-35 | R = —⌬—O—⌬ |
| M-36 | R = —⌬—OCH$_2$CH$_2$CH(CH$_3$)CH$_3$ |

TABLE 4

Fluorene Polymers

| Polymer | Diboronate (mole %) | Dibromide (mole %) | yield (%) | h_inh, dL/g solvent | Film Absorption Peaks (nm) | Film PL Peaks (nm) | Emission Color |
|---|---|---|---|---|---|---|---|
| P-1 | M-28 (100) | M-1 (100) | 92 | 1.0 THF | 379 | 425, 443, 479 | Blue |
| P-2 | M-30 (100) | M-3 (100) | 94 | 1.0 THF | 379 | 433, 446, 479 | Blue |
| P-3 | M-33 (100) | M-8 (100) | 58 | 0.6 CHCl₃ | 387, 406 | 432, 447, 482 | Blue |
| P-4 | M-30 (100) | M-9 (100) | 75 | 0.7 Toluene | | | Blue |
| P-5 | M-30 (100) | M-11 (100) | 90 | | 435, 461 | 502, 534 | Green |
| P-6 | M-30 (100) | M-12 (100) | 82 | 1.8 THF | 445 | 509, 543, 580 | Yellow |
| P-7 | M-30 (100) | M-20 (100) | 50 | 0.3 THF | 365 | 456, 482 | Blue |
| P-8 | M-30 (100) | M-14 (100) | 78 | 0.4 THF | 345 | 430 (Film) | Blue |
| P-9 | M-35 (100) | M-14 (100) | 85 | 0.5 Toluene | 368 | 430 | Blue |
| P-10 | M-30 (100) | M-15 (100) | 87 | 1.1 THF | 322, 450 | 546 | Yellow-Green |
| P-11 | M-30 (100) | M-17 (100) | 92 | 0.7 THF | 334, 438 | | Green |
| P-12 | M-30 (100) | M-23 (100) | 83 | 0.4 THF | 385 | 432, 457 | Green |
| P-13 | M-30 (50) M-29 (50) | M-11 (100) | 65 | | 436, 463 | | Green |
| P-14 | M-31 (67) M-29 (33) | M-11 (100) | 85 | 1.2 Toluene | 461, 435 | 483, 512, 548 | Green |
| P-15 | M-32 (67) M-29 (33) | M-11 (100) | 85 | 0.6 THF | 460, 434 | 483, 512, 544 | Green |
| P-16 | M-31 (67) M-29 (33) | M-18 (100) | 93 | 1.0 THF | | | Blue |
| P-17 | M-30 (67) M-35 (33) | M-11 (100) | 69 | 1.0 THF | | | Green |
| P-18 | M-30 (67) M-35 (33) | M-12 (100) | 82 | 1.5 THF | 457, 480 | | Yellow |
| P-19 | M-31 (67) M-29 (33) | M-24 (100) | 43 | 0.5 THF | | | Blue |
| P-20 | M-30 (100) | M-3 (95) M-11 (5) | 97 | 0.9 THF | | | Blue |
| P-21 | M-30 (100) | M-2 (18) M-11 (82) | 50 | 0.3 THF | | | Green |
| P-22 | M-30 (100) | M-3 (50) M-24 (50) | 57 | 0.6 THF | | | Blue |
| P-23 | M-30 (100) | M-13 (17) M-11 (83) | 75 | 0.6 THF | | | Green |
| P-24 | M-30 (100) | M-3 (60) M-22 (40) | 93 | 0.6 Toluene | 389 | 519 | Green |
| P-25 | M-30 (100) | M-3 (90) M-22 (10) | 73 | 0.7 THF | 388 | 491 | Green |
| P-26 | M-30 (100) | M-3 (95) M-22 (5) | 81 | 0.9 THF | 381 | 489, 508 | Green |
| P-27 | M-30 (100) | M-3 (67) M-22 (33) | 58 | 0.6 Toluene | 387 | 512 | Green |
| P-28 | M-32 (50) | M-3 (47.5) M-22 (2.5) | 90 | 1.3 THF | 387 | 479, 500 | Green |
| P-29 | M-30 (100) | M-3 (95) M-19 (5) | 90 | 1.4 THF | 386 | 545 | Yellow |
| P-30 | M-32 (67) M-30 (33) | M-2 (33) M-22 (67) | 94 | 0.9 THF | 423 | 524 | Green |
| P-31 | M-32 (67) M-29 (33) | M-2 (33) M-21 (67) | 75 | 0.5 THF | | | Green |
| P-32 | M-30 (100) | M-25 | 95 | 0.42 THF | | | Blue |
| P-33 | M-30 (100) | M-26 | 95 | | | | Blue |
| P-34 | M-30 (100) | M-27 | 95 | 1.84 THF | | | Blue |

EXAMPLE 35

Electroluminescent Devices

The ITO-glass used for device fabrication has a nominal sheet resistance of 15 ohm/square. The hole injection conducting polymer when used is PEDT (see page 8), the hole-transporting polymer when used is poly(4,4'-biphenylene-diyl-N'N'-diphenyldiamino-1,4-phenylene) described in U.S. patent application Ser. No. 08/696,281, filed on Aug. 13, 1996, hereinafter abbreviated as "P3DA", and the electron-transporting layer when used is the aluminum complex of 8-hydroxy-quinoline hereinafter abbreviated as "Alq". Films of PEDT are formed by spin coating from aqueous solutions of the polymer obtained from Bayer Corporation. Films of P3DA are formed by spin coating from chlorobenzene solutions. Alq films are formed by thermal evaporation in high vacuum. Multi-layer devices are fabricated by laying down the layers sequentially starting from the layer next to the ITO. After all the layers have been deposited, the appropriate metallic cathodes are then deposited on top of the organic film by thermal evaporation. Magnesium alloys in this instance are alloys of magnesium containing at least 85 percent of magnesium.

Completed devices are connected to a power source and are driven with a positive bias, that is, making the ITO as the positive electrode. The electric field (megavolt/cm or MV/cm) and the current density (mA/cm$^2$) required to generate 100 Cd/m$^2$ of light output are used to characterize the performance of a device. Results for representative devices are given in Table 5.

What is claimed is:

1. A polymer comprising repeat units of the formula:

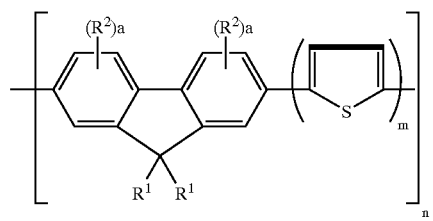

wherein $R^1$ is independently in each occurrence $C_{1-20}$ hydrocarbyl or C1-20 hydrocarbyl containing one or more heteroatoms of S, N, O, P or Si or both $R^1$ may form, with the 9-carbon of the fluorene ring, a $C_{5-20}$ ring structure containing one or more heteroatoms of S, N, or O; $R^2$ is independently in each occurrence $C_{1-20}$ hydrocarbyl, $C_{1-20}$ hydrocarbyloxy, $C_{1-20}$ thioether, $C_{1-20}$ hydrocarbyloxycarbonyl, hydrocarbylcarbonyloxy, or cyano; a is independently in each occurrence a number from about 0 to about 1;

m is a number from about 1 to about 2; and n is a number from about 3 or greater.

2. The polymer of claim 1 wherein $R^1$ is independently in each occurrence an alkyl of $C_{1-12}$.

3. The polymer of claim 1 wherein n is a number of at least 10.

4. The polymer of claim 1 wherein n is a number of at least 30.

TABLE 5

Electroluminescent Devices

| Device No | Hole Injection | Hole Transport | Fluorene Polymer[1] | Electron Transport | Cathode | E (mV/cm) to 100 Cd/m$^2$ | J (mA/cm$^2$) to 100 Cd/m$^2$ |
|---|---|---|---|---|---|---|---|
| D-1 | — | — | P-14 | | Mg alloy | 2.7 | 10 |
| D-2 | — | — | P-14 | Alq | Mg Alloy | 1.0 | 8 |
| D-3 | PEDT | — | P-14 | Alq | Mg Alloy | 0.73 | 20 |
| D-4 | — | P3DA | P-14 | — | Al | 0.8 | 35 |
| D-5 | — | P3DA | P-14 | Alq | Mg Alloy | 0.6 | 6 |
| D-6 | — | PVK[2] | P-14 | Alq | Mg Alloy | 1.0 | 10 |
| D-7 | — | P3DA | P-1 | — | Ca | 1.1 | 40 |
| D-8 | — | P3DA | P-10 | — | Mg Alloy | 0.7 | 40 |
| D-9 | — | P3DA | 90% P-1 10% P-10 | — | Mg Alloy | 0.6 | 6 |
| D-10 | — | — | P-26 | — | Ca | 2.5 | 18 |
| D-11 | — | P3DA | P-26 | — | Ca | 1.9 | 100 |
| D-12 | — | — | P-26 | — | Al | 2.2 | 20 |
| D-13 | — | — | P-25 | — | Al | 2 | 30 |
| D-14 | — | — | P-24 | — | Al | 1.7 | 40 |
| D-15 | — | P3DA | P-27 | — | Al | 1.4 | 20 |
| D-16 | — | P3DA | P-30 | — | Al | 0.8 | 45 |
| D-17 | PEDT | PVK | P-26 | — | Al | 0.9 | 90 |
| D-18 | — | P3DA | 90% P-1 10% P-11 | — | Mg Alloy | 0.9 | 15 |
| D-19 | PEDT | PVK | P-27 | — | Al | 0.75 | 70 |

[1]The fluorene polymer numbers refer to polymers of Table 4.
[2]PVK = polyvinylcarbazole 5. The polymer of claim 1 comprising units represented by the formula:
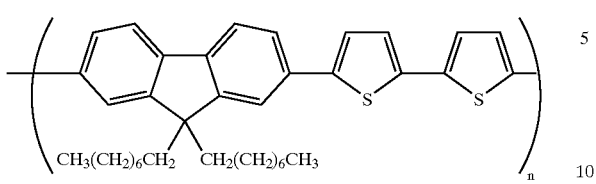
6. The polymer of claim 1 comprising units represented by the formula:
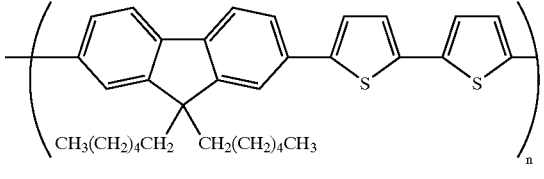
* * * * *